US012723954B2

(12) United States Patent
Ilhamsyah et al.

(10) Patent No.: US 12,723,954 B2
(45) Date of Patent: Sep. 1, 2026

(54) VAPOR ANALYZERS AND VAPOR ANALYSIS SYSTEMS AND METHODS

(71) Applicant: Georgia Tech Research Corporation, Atlanta, GA (US)

(72) Inventors: Rizky Ilhamsyah, Atlanta, GA (US); Peter J. Hesketh, Atlanta, GA (US); Jean-Marie D. Dimandja, Atlanta, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 343 days.

(21) Appl. No.: 18/684,368

(22) PCT Filed: Sep. 8, 2022

(86) PCT No.: PCT/US2022/076113
§ 371 (c)(1),
(2) Date: Feb. 16, 2024

(87) PCT Pub. No.: WO2023/039473
PCT Pub. Date: Mar. 16, 2023

(65) Prior Publication Data

US 2024/0426720 A1 Dec. 26, 2024

Related U.S. Application Data

(60) Provisional application No. 63/241,726, filed on Sep. 8, 2021.

(51) Int. Cl.
*G01N 1/40* (2006.01)
*G01N 33/497* (2006.01)

(52) U.S. Cl.
CPC ......... *G01N 1/4022* (2013.01); *G01N 33/497* (2013.01)

(58) Field of Classification Search
CPC ......... G01N 1/4022; G01N 2001/4033; G01N 33/497; G01N 33/4972; G01N 33/4975; A61B 5/082; A61B 5/097
See application file for complete search history.

(56) References Cited

U.S. PATENT DOCUMENTS

| | | | | |
|---|---|---|---|---|
| 4,494,380 A * | 1/1985 | Cross | F01N 3/00 62/3.2 |
| 2018/0209946 A1 | 7/2018 | Chou et al. | |
| 2020/0060750 A1 | 2/2020 | Kaveckis et al. | |

FOREIGN PATENT DOCUMENTS

| | | | |
|---|---|---|---|
| WO | WO-2012010281 A1 * | 1/2012 | G01N 33/0014 |

OTHER PUBLICATIONS

Machine translation of WO 2012010281 (Year: 2012).*
International Search Report and Written Opinion from Application No. PCT/US2022/076113 dated Nov. 25, 2022.

* cited by examiner

*Primary Examiner* — Nathaniel J Kolb
(74) *Attorney, Agent, or Firm* — TROUTMAN PEPPER LOCKE LLP; Ryan A. Schneider; Korbin M. Blunck

(57) ABSTRACT

Disclosed herein are vapor analyzer systems comprising a chamber defining an interior channel, an inlet in fluid communication with the interior channel, a liquid phase outlet in fluid communication with the interior channel, a vapor phase outlet in fluid communication with the interior channel, and a cooling plate disposed along at least a portion of the interior channel within the chamber. The liquid phase outlet and the inlet can define a first fluid flow path from the inlet, through the interior channel, to the liquid phase outlet. The vapor phase outlet and the inlet can define a second fluid flow path from the inlet, through the interior channel to the vapor phase outlet. Each of the first fluid flow path and the second fluid flow path can contact the cooling plate.

14 Claims, 19 Drawing Sheets

Channel cross section

Subcooled Wall

100

VAPOR ANALYZERS AND VAPOR ANALYSIS SYSTEMS AND METHODS

CROSS-REFERENCE TO RELATED APPLICATIONS

This application claims the benefit of U.S. Provisional Application Ser. No. 63/241,726, filed on 8 Sep. 2021, the entire contents and substance of which are incorporated herein by reference in their entirety as if fully set forth below.

FIELD OF THE DISCLOSURE

The present disclosure relates generally to vapor analysis systems and methods. Particularly, embodiments of the present disclosure relate to liquid and vapor phase separation of a vapor sample for analysis.

BACKGROUND

Vapor analysis can be a promising alternative for non-invasive health diagnosis. Traces of certain organic compound presented in vapors such as exhaled breath can be a biomarker for various diseases. There are two vapor collection methods, particularly for the example of breath collection methods, that are commonly used in practice: gas portion collection, mostly for Volatile Organic Compounds (VOCs), and liquid portion collection, for Exhaled Breath Condensate (EBC). In gas portion collection, the patient can exhale through a gas sample container such as Tedlar bag, steel canister, or glass tube. Depending on the need, a preconcentrator, device, such as SPME or Thermal Desorption tube, can be introduced to the gas container to amplify the concentration of trace level biomarker in the breath sample. The collected breath sample can then be measured by using gas chromatography, laser spectroscopy, or other relevant techniques. On the other hand, in liquid portion collection, the patient can exhale through a subcooled tube. Since exhaled breath can be rich in water vapor, some of this vapor can condense along with less volatile organic compounds, such as protein and nucleic acids. This condensate can then be collected and further analyzed using liquid chromatography or immunoassays or biosensors or by chemical derivitization prior to GC-MS analysis.

For both methods, effective extraction of water vapor from the breath sample can be a desirable aspect. In gas phase collection, dehumidification can be used because high moisture content in a breath sample might have an adverse effect to the measurement of VOC concentration. For example, uncontrolled condensation of water vapor in the gas container can cause variation in measured VOC profiles. On the other hand, some pre-concentrator used for absorbing the trace VOC, such as Tenax and carboxen, can be hydrophilic and can absorb lower amounts of VOC in presence of moisture. In the liquid portion collection, effective water extraction can be used to reduce the EBC collection time. The more water vapor extracted from gas sample; the less amount of exhalation cycle can be needed to provide a sufficient amount of sample. Condensate collection time lower than 10 minutes can be used for breath comfort.

What is needed, therefore, are vapor analysis systems and methods that can separate liquid and vapor phase components for analysis. Embodiments of the present disclosure address this need as well as other needs that will become apparent upon reading the description below in conjunction with the drawings.

BRIEF SUMMARY OF THE DISCLOSURE

The present disclosure relates generally to vapor analysis systems and methods. Particularly, embodiments of the present disclosure relate to liquid and vapor phase separation of a vapor sample for analysis.

An exemplary embodiment of the present disclosure can provide a vapor analyzer comprising: a chamber defining an interior channel; an inlet in fluid communication with the interior channel; a liquid phase outlet in fluid communication with the interior channel, the liquid phase outlet and the inlet defining a first fluid flow path from the inlet, through the interior channel, to the liquid phase outlet; a vapor phase outlet in fluid communication with the interior channel, the vapor phase outlet and the inlet defining a second fluid flow path from the inlet, through the interior channel to the vapor phase outlet; and a cooling plate disposed along at least a portion of the interior channel within the chamber such that the first fluid flow path and the second fluid flow path contact the cooling plate.

In any of the embodiments disclosed herein, the first fluid flow path and the second fluid flow path can be contained together within the chamber.

In any of the embodiments disclosed herein, the first fluid flow path and the second fluid flow path can be parallel.

In any of the embodiments disclosed herein, the cooling plate can comprise a Peltier cooler.

In any of the embodiments disclosed herein, the liquid phase outlet can be disposed on a surface of the chamber to create an exit from the interior channel, and the cooling plate and the liquid phase outlet can share the same surface in the chamber.

In any of the embodiments disclosed herein, the cooling plate can be maintained at a temperature sufficient to condense water vapor from a vapor phase into a liquid phase.

In any of the embodiments disclosed herein, the cooling plate can achieve a water vapor removal efficiency of 50% or greater.

In any of the embodiments disclosed herein, the vapor analyzer can further comprise a sensor attached to the inlet and configured to measure fluid properties along the first fluid flow path and the second fluid flow path.

In any of the embodiments disclosed herein, the vapor analyzer can further comprise a controller in communication with the sensor and connected to the cooling plate, the controller configured to alter the cooling plate between an active state and an inactive state, and the cooling plate can be providing cooling energy to the interior channel in the active state.

In any of the embodiments disclosed herein, the controller can place the cooling plate in the active state responsive to the sensor detecting a particle for detection.

Another embodiment of the present disclosure can provide a vapor analysis method comprising: feeding an analyte to a chamber defining an interior channel through an inlet in fluid communication with the interior channel, the analyte being in the vapor phase; contacting the analyte with a cooling plate disposed along at least a portion of the interior channel within the chamber; condensing a portion of the analyte into a liquid portion as a result of contact with the cooling plate, the remainder of the analyte being in a vapor portion; and transferring the liquid portion along a first fluid flow path to a liquid phase outlet and the vapor portion along a second fluid flow path to a vapor phase outlet, the liquid phase outlet and the vapor phase outlet each in fluid communication with the interior channel.

In any of the embodiments disclosed herein, the first fluid flow path and the second fluid flow path can be contained together within the chamber.

In any of the embodiments disclosed herein, the first fluid flow path and the second fluid flow path can be parallel.

In any of the embodiments disclosed herein, the cooling plate can comprise a Peltier cooler.

In any of the embodiments disclosed herein, the liquid phase outlet can be disposed on a surface of the chamber to create an exit from the interior channel, and the cooling plate and the liquid phase outlet can share the same surface in the chamber.

In any of the embodiments disclosed herein, the cooling plate can be maintained at a temperature sufficient to condense water vapor from a vapor phase into a liquid phase.

In any of the embodiments disclosed herein, the cooling plate can achieve a water vapor removal efficiency of 50% or greater.

In any of the embodiments disclosed herein, the vapor analyzer can further comprise a sensor attached to the inlet and configured to measure fluid properties along the first fluid flow path and the second fluid flow path.

In any of the embodiments disclosed herein, the vapor analyzer can further comprise a controller in communication with the sensor and connected to the cooling plate, the controller configured to alter the cooling plate between an active state and an inactive state, and the cooling plate can be providing cooling energy to the interior channel in the active state.

In any of the embodiments disclosed herein, the controller can place the cooling plate in the active state responsive to the sensor detecting a particle for detection.

These and other aspects of the present disclosure are described in the Detailed Description below and the accompanying figures. Other aspects and features of embodiments of the present disclosure will become apparent to those of ordinary skill in the art upon reviewing the following description of specific, exemplary embodiments of the present invention in concert with the figures. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments of the invention discussed herein. In similar fashion, while exemplary embodiments may be discussed below as device, system, or method embodiments, it is to be understood that such exemplary embodiments can be implemented in various devices, systems, and methods of the present disclosure.

BRIEF DESCRIPTION OF THE DRAWINGS

The accompanying drawings, which are incorporated in and constitute a part of this specification, illustrate multiple embodiments of the presently disclosed subject matter and serve to explain the principles of the presently disclosed subject matter. The drawings are not intended to limit the scope of the presently disclosed subject matter in any manner.

DETAILED DESCRIPTION

Figure 1A:
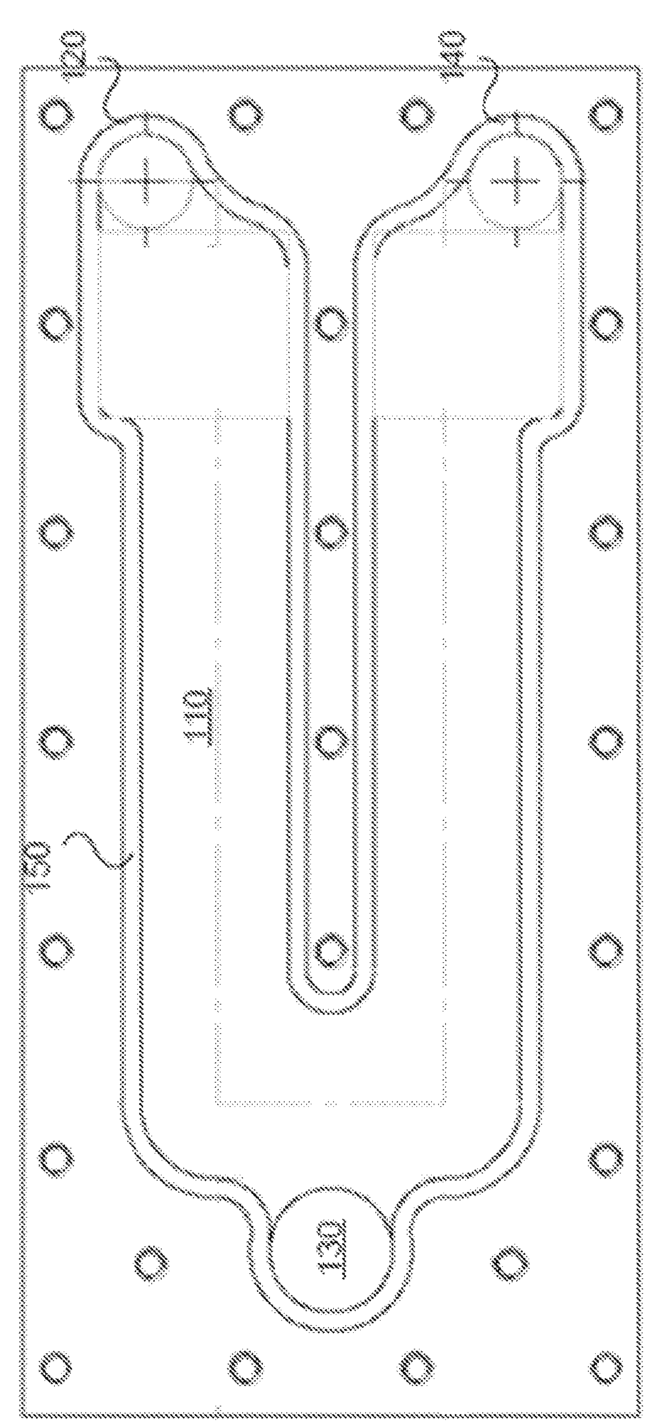
FIGS. 1A & 1B illustrate examples of a vapor analyzer in accordance with the present disclosure.

Breath analysis can be desirable for noninvasive health diagnostics method by detecting disease biomarkers. However, the exhaled breath collection process can be a challenge. Specifically, the effective separation of the water vapor from the breath sample, which can be used to avoid humidity interference in gas detection system and to preserve the liquid condensate for other analysis, is desirable. Disclosed herein is an analytical model that can obtain the optimized condenser for a portable breath collection system to effectively provide both a dry gas phase sample and an exhaled breath condensate. The mathematical model can be verified by using a heated water bubbler as warm and humid air generator (in vitro). Furthermore, the performance of the device can be tested by using actual human breath (in vivo). The temperature and moisture concentration values can have a good agreement with the measured values with margin of error±15%, and ±30% for an amount of collected condensate. The in vivo result shows, with the thermoelectric element cooled up to 8.5° C., a moisture removal efficiency of 62.4% or greater can be achieved. As disclosed herein, the system can collect exhaled breath condensate of 0.457±0.092 ml and dry gas (RH 47.8% at 27° C.) for 10 exhalations.

The need for effective extraction of water vapor from the gas portion of a breath sample and the need to collect both gas and liquid portions of a breath sample for comprehensive breath diagnosis, can utilize a well-designed condenser to be part of breath collection system. Disclosed herein is a mathematical model to parametrically simulate the condensation process in the breath collection system and a breath collection device for simultaneous dry gas sample and liquid condensate; aiming to have high removal efficiency, rapid collection, breath comfort, and miniaturization for point-of-care application.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or carried out in various ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter.

Reference will now be made in detail to exemplary embodiments of the disclosed technology, examples of which are illustrated in the accompanying drawings and disclosed herein. Wherever convenient, the same references numbers will be used throughout the drawings to refer to the same or like parts.

Figure 1B:
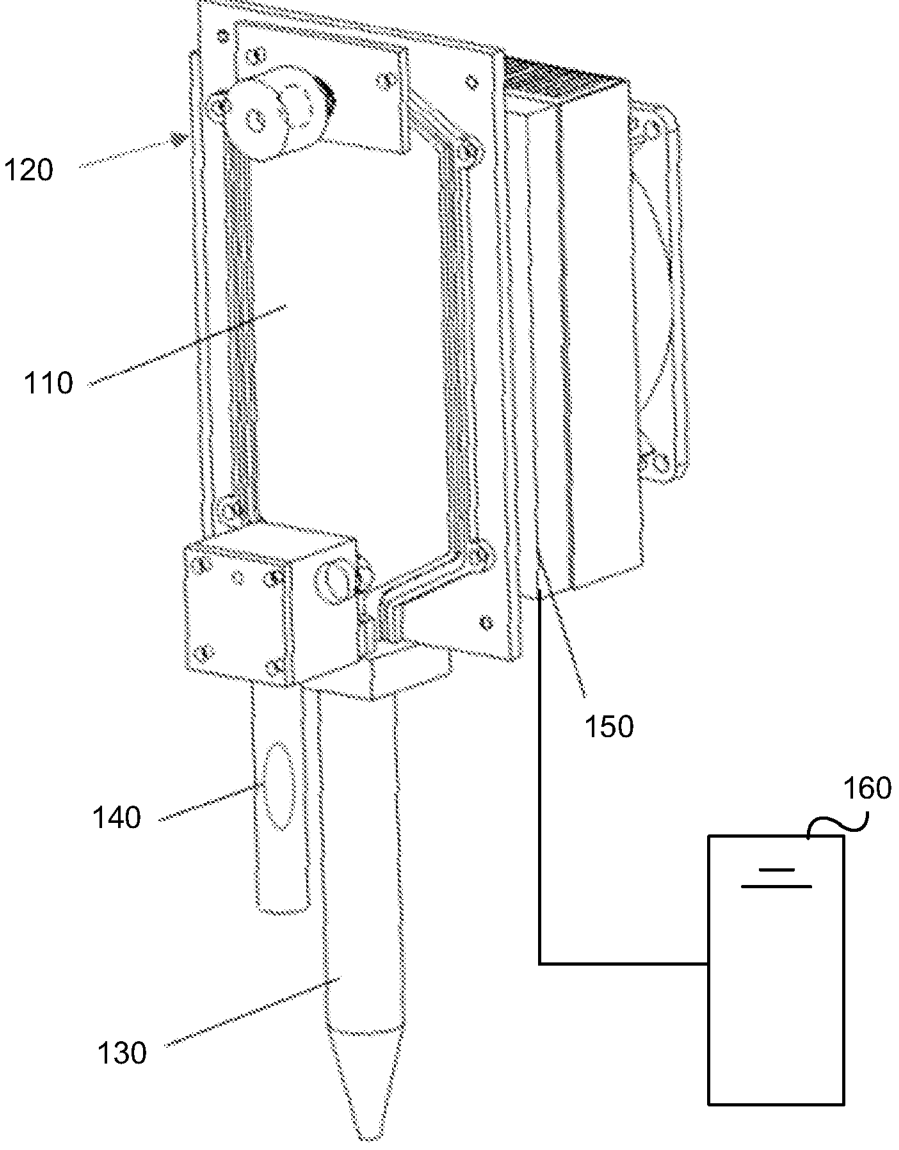

FIGS. 1A and 1B illustrate a vapor analyzer 100 which can be used in a vapor analysis system. As shown, the vapor analyzer 100 can comprise a chamber 110 that defines an interior channel within the vapor analyzer 100. The chamber 110 can have a variety of geometries. The chamber 110 can be configured such that the interior channel has a desired surface area. The chamber 110 can further be made from any material configured to confer particular material properties to the interior channel. For instance, the chamber 110 can be made from a hydrophobic material to improve droplet movement in the interior channel. The chamber 110 need not be made from a hydrophobic material or other material to confer specific material properties thereto. The chamber 110 can comprise a coating. For example, the chamber 110 can comprise a hydrophobic coating, an anti-corrosive coating, and the like.

The vapor analyzer 100 can further comprise an inlet 120 that can fluidly communicate with the interior channel. In other words, the inlet 120 can be an aperture that leads to the chamber 110. The inlet 120 can be configured to a receive a sample and/or analyte to be fed into the interior chamber. The inlet 120 can further include a sealant to protect the inlet 120 from intrusions of outside contaminants from the environment surrounding the vapor analyzer 100, such as gaskets, O-rings, adhesives, and the like.

The inlet 120 can include sensors for detecting various properties of samples fed through the inlet 120. For example, the sensors can include a humidity sensor, a carbon dioxide sensor, a pressure sensor, a flow rate sensor, and the like. The sensors can measure such properties of a material being passed through the inlet 120 into the interior channel.

The vapor analyzer 100 can further comprise a liquid phase outlet 130 that can fluidly communicate with the interior channel. In other words, the liquid phase outlet 130 can be an aperture that exits the chamber 110. The liquid phase outlet 130 can be configured to receive material from within the interior chamber and allow such material to pass therethrough to exit the vapor analyzer 100. The liquid phase outlet 130 can further include a sealant to protect the liquid phase outlet 130 from intrusions of outside contaminants from the environment surrounding the vapor analyzer 100, such as gaskets, O-rings, adhesives, and the like.

The liquid phase outlet 130 can be disposed on a surface of the chamber 110 to create an exit from the interior channel for any liquid that may be contained in the interior channel. The liquid phase outlet 130 can encourage liquid flow therethrough by any number of methods. For example, the liquid phase outlet 130 can be positioned on a bottom surface of the chamber 110 such that gravity can pull liquid contents from the interior channel through the liquid phase outlet 130. Other methods can be used in conjunction with the liquid phase outlet 130, such as pumps or other fluid movers. In such an example, the liquid phase outlet 130 need not be on a bottom surface, but can be on any surface of the chamber 110.

The vapor analyzer 100 can further comprise a vapor phase outlet 140 that can fluidly communicate with the interior channel. In other words, the vapor phase outlet 140 can be an aperture that exits the chamber 110. The vapor phase outlet 140 can be configured to receive material from within the interior chamber and allow such material to pass therethrough to exit the vapor analyzer 100. The vapor phase outlet 140 can further include a sealant to protect the vapor phase outlet 140 from intrusions of outside contaminants from the environment surrounding the vapor analyzer 100, such as gaskets, O-rings, adhesives, and the like.

The vapor phase outlet 140 can be disposed on a surface of the chamber 110 to create an exit from the interior channel for any vapor that may be contained in the interior channel. The vapor phase outlet 140 can share a surface with the liquid phase outlet 130. Alternatively, the vapor phase outlet 140 can be on a separate surface from the liquid phase outlet 130. Further, the vapor phase outlet 140 can be positioned at a greater distance away from the inlet 120 when compared to the liquid phase outlet 130. In other words, material can travel through the interior channel for a longer residence time to reach the vapor phase outlet 140 compared to the liquid phase outlet 130.

In such a manner, the inlet 120, the liquid phase outlet 130, and the vapor phase outlet 140 can create a first fluid flow path and a second fluid flow path. The first fluid flow path can flow through the interior channel from the inlet 120 to the liquid phase outlet 130. The second fluid flow path can flow through the interior channel from the inlet 120 to the vapor phase outlet 140. Both the first and second fluid flow path can be contained within the chamber 110. The chamber 110 can comprise a first and second interior channel corresponding to the first and second fluid flow path. Alternatively, the first and second fluid flow path can be contained within the same interior channel within the chamber 110. In such a manner, the first and second fluid flow path can be in parallel.

The liquid phase outlet 130 and the vapor phase outlet 140 can also include sensors, as with the inlet 120, for detecting various properties of samples fed therethrough. For example, the sensors can include a humidity sensor, a carbon dioxide sensor, an oxygen sensor, a VOC sensor, a temperature sensor, a pressure sensor, a flow rate sensor, and the like. The sensors can measure such properties of a material being passed through the liquid phase outlet 130 and the vapor phase outlet 140 to exit the chamber 110. The sensors at the liquid phase outlet 130 and the vapor phase outlet 140 can further be configured to detect specific compounds of interest such as carbon dioxide, nitric oxide, hydrogen, oxygen, hydrogen sulfide, ammonia, acetone, or other volatile components to help with disease condition monitoring or as a rapid test.

The vapor analyzer 100 can further comprise a cooling plate 150 disposed along at least a portion of the interior channel and within the chamber 110. The cooling plate 150 can be positioned such that the first and second fluid flow path come into contact with the cooling plate 150 while passing through the interior channel. The cooling plate 150 can be any surface and/or material configured to change temperatures. For example, the cooling plate 150 can be maintained at a temperature sufficient to condense water vapor. The cooling plate 150 can comprise a heat sink configured to remove heat energy from the chamber 110. For example, the cooling plate 150 can comprise a Peltier cooler, a heat exchanger, a miniaturized heat exchanger, a refrigerator, dry ice, liquid nitrogen, liquid oxygen, and the like.

In such an example, the cooling plate 150 can be configured to achieve a water vapor removal efficiency of 50% or greater (e.g., 55% or greater, 60% or greater, 65% or greater, 70% or greater, 75% or greater, 80% or greater, 85% or greater, 90% or greater, or 95% or greater) based on an initial concentration of water vapor in the sample fed to the inlet 120. The cooling plate 150 can be configured to achieve a water vapor removal efficiency from 50% to 100% (e.g., from 55% to 95%, from 60% to 90%, from 60% to 85%, from 60% to 80%, from 60% to 75%, from 60% to 70%, from 60% to 65%, from 65% to 85%, from 70% to 80%, from 65% to 90%, from 70% to 90%, from 75% to 90%, or from 80% to 90%) based on an initial concentration of water vapor in the sample fed to the inlet 120.

The vapor analyzer 100 can further comprise a controller 160. The controller 160 can be connected to and/or in communication with the sensors on the inlet 120, the liquid phase outlet 130, and/or the vapor phase outlet 140. The controller 160 can further be connected to and/or in communication with the cooling plate 150. The controller 160 can alter the cooling plate 150 between an active state and an inactive state. The cooling plate 150 can be providing cooling energy (e.g., removing heat energy) from the interior channel in the active state.

The transition from the inactive state to the active state can be conducted in response to a sensor detecting a particular property in the sample fed to the inlet 120. For example, the controller 160 can activate the cooling plate 150 if a carbon dioxide sensor at the inlet 120 detects a carbon dioxide concentration at a particular value, or the controller 160 can activate the cooling plate 150 if a pressure sensor at the inlet 120 detects a pressure drop at a particular value. The transition from the inactive state to the active state can further be conducted in response to a sensor detecting the presence of a particular particle or molecule in the sample fed to the inlet 120.

Figure 2:
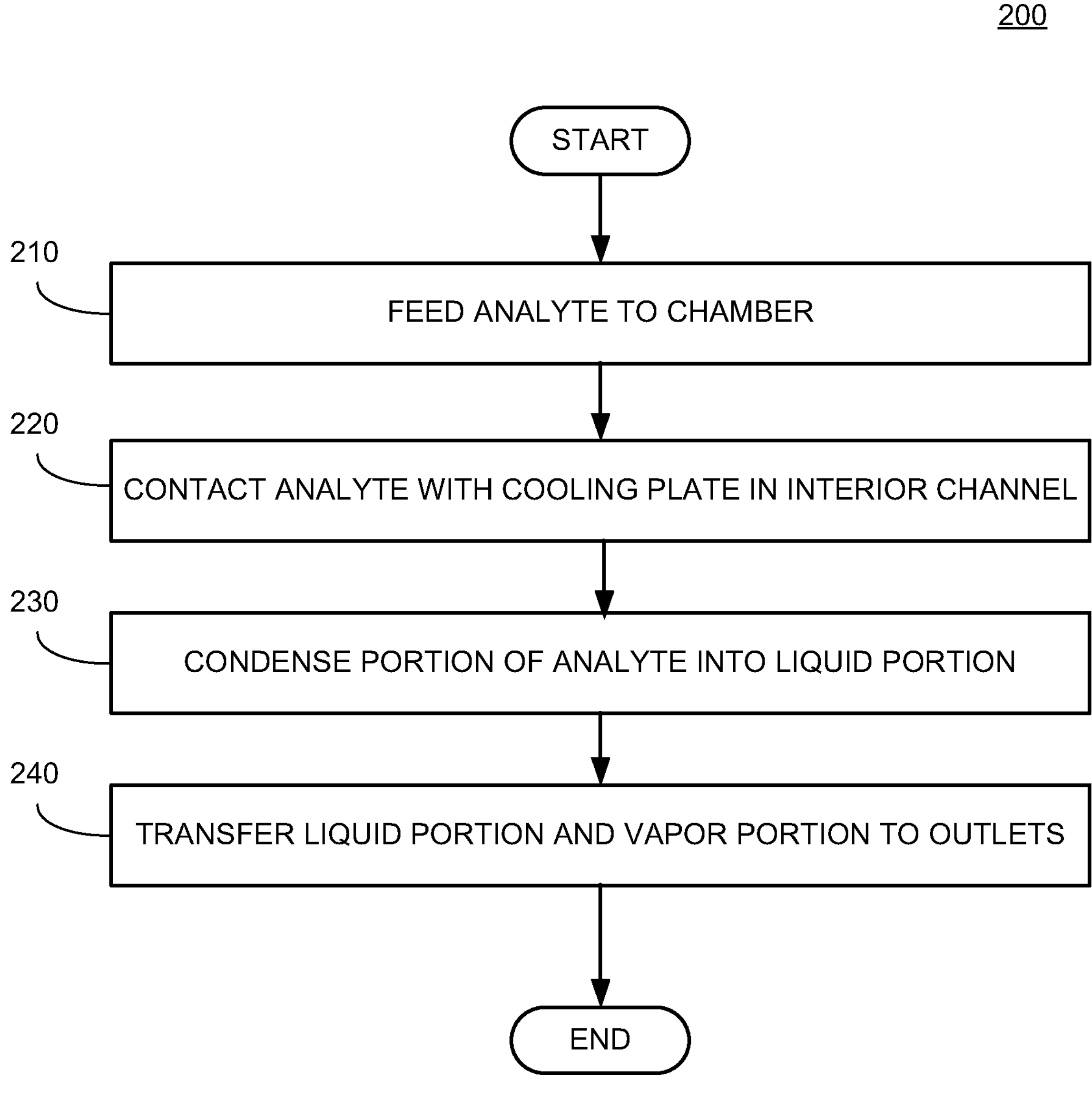
FIG. 2 illustrates a flowchart of a vapor analysis method in accordance with the present disclosure.

FIG. 2 is a flowchart of a vapor analysis method 200. Although the method is described with respect to the vapor analyzer 100, it is understood that this is merely an illustrative example of the flow of the method 200. It should be understood that the method 200 can be implemented with a variety of vapor analyzers and vapor analysis systems.

As shown in block 210, the method 200 can comprise feeding an analyte to the chamber 110 defining the interior channel. The analyte can be fed through the inlet 120 in fluid communication with the interior channel. The analyte can also be in the vapor phase. The analyte can be, for example, a human breath, and the human breath can be exhaled into the inlet 120. The method 200 can then proceed on to block 220.

In block 220, the method 200 can comprise contacting the analyte with the cooling plate 150 disposed along at least a portion of the interior channel within the chamber 110. For the example of a human breath, the breath sample can traverse the interior channel while contacting the cooling plate 150. The cooling plate 150 can bring the human breath to below saturation temperature.

In some examples, the controller 160 can activate the cooling plate 150 after a certain amount of time and/or in response to a sensor at the inlet 120 detecting certain properties in the analyte. For the example of a human breath, the sensor at the inlet 120 can detect material indicative of a portion of the breath sample received from deep inside a user's lungs. In response, the controller 160 can activate the cooling plate 150 to condense water vapor from such a portion of the breath sample to isolate desirable material in the breath sample. The method 200 can then proceed on to block 230.

In block 230, the method 200 can comprise condensing a portion of the analyte into a liquid portion. The condensing can occur as a result of the contact with the cooling plate 150. The remainder of the analyte not condensed can remain in a vapor portion. For the example of a human breath, bring the breath sample below saturation temperature can cause water vapor in the breath to condense into liquid form while other substances in the breath remain in vapor form. The method 200 can then proceed on to block 240.

In block 240, the method 200 can comprise transferring the liquid portion along the first fluid flow path to the liquid phase outlet 130. The vapor portion can be transferred along the second fluid flow path to the vapor phase outlet 140. The liquid phase outlet 130 and the vapor phase outlet 140 can each be in fluid communication with the interior channel. In some examples, the first and second fluid flow path can be contained within the same interior channel. The method 200 can be terminated after block 240. However, in some examples, the method 200 can continue on to other method steps contemplated herein but not shown.

Certain embodiments and implementations of the disclosed technology are described above with reference to block and flow diagrams of systems and methods and/or computer program products according to example embodiments or implementations of the disclosed technology. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, may be repeated, or may not necessarily need to be performed at all, according to some embodiments or implementations of the disclosed technology.

EXAMPLES

The following examples are provided by way of illustration but not by way of limitation.

Figure 3:
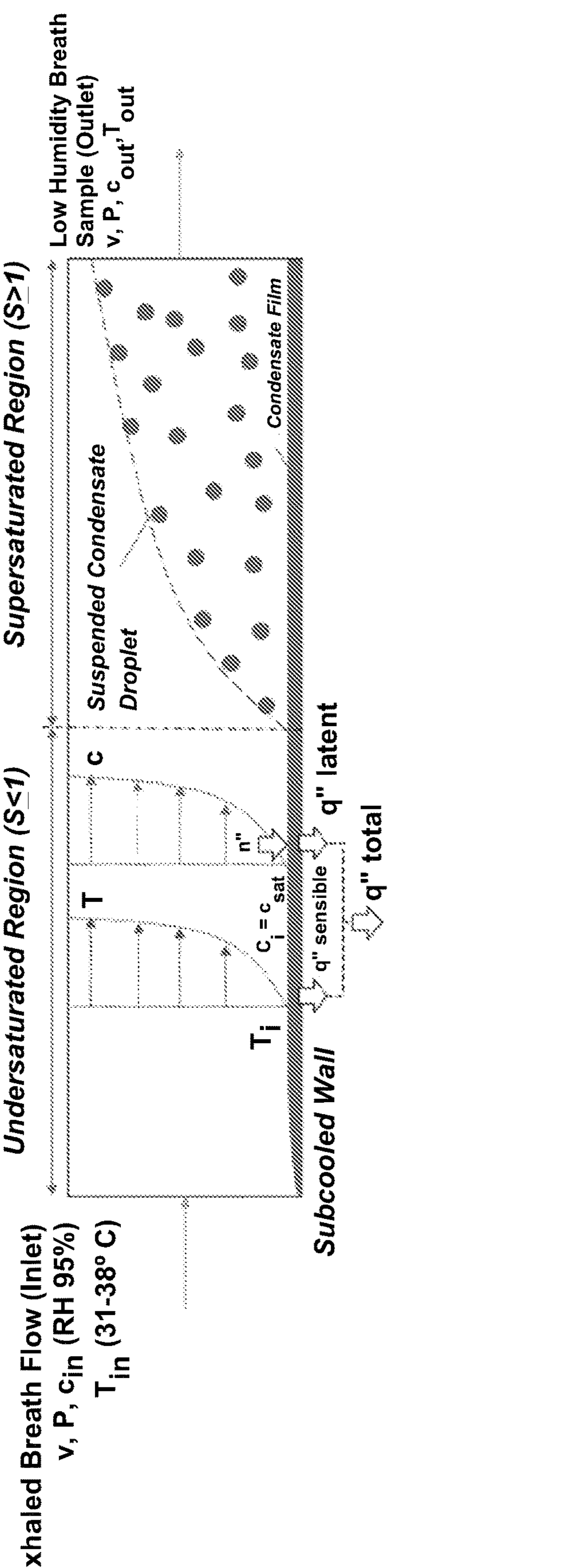
FIG. 3 illustrates a channel of a vapor analysis system in accordance with the present disclosure.

Consider a gas phase fluid of exhaled breath sample, containing a water vapor as dilute species, flowing through a channel with a subcooled wall as shown in FIG. 3. The incoming breath sample can be parametrically identified using four parameters: gas mixture velocity (v), gas mixture pressure (P), gas mixture temperature (T), and concentration of dilute species (c). Within the channel, the gas mixture can be cooled down below dew point temperature of the dilute species and condensation starts. The mechanism of this condensation can depend on whether the bulk dilute species is undersaturated or supersaturated, which can be parametrically identified by a saturation ratio(S). The supersaturation ratio can be defined as ratio between partial vapor pressure ($P_v$) and saturated vapor pressure ($P_{sat}$) of the dilute species, the mixture can be undersaturated if S<1 and supersaturated if S>1. In an undersaturated region, the bulk temperature of gas mixture can be higher than the dew point temperature of the dilute species. In this zone, the condensation can occur due to diffusion of vapor phase dilute species onto the subcooled wall and form a thin condensate film. The supersaturation region can potentially be reached if the heat diffuses faster than the mass of dilute species. The bulk temperature of the gas mixture can drop below the dew point temperature of the dilute species, and a dispersed droplet can form. Without wishing to be bound by any particular scientific theory, the deposition of condensate on the wall in this zone can be driven by vapor phase diffusion and droplet particle diffusion.

A set of differential equations can be arranged to simultaneously solve the gas mixture velocity (v), Pressure (P), water vapor concentration (c), and gas mixture temperature (T). Four governing differential equations used to solve these parameters can be: Mass conservation equation, Navier-Stokes's equation, Heat Diffusion equation, and Dilute Species Transport equation:

$$\frac{\partial \rho_m}{\partial t} + \nabla . (\rho \vec{v}) = 0 \quad (1)$$

$$\frac{\partial}{\partial t}(\rho_m \vec{v}) + \vec{v}\nabla \cdot (\rho_m \vec{v}) = -\nabla P + \mu \nabla^2 \vec{v} \quad (2)$$

$$\rho_m C_p\left(\frac{\partial T}{\partial t} + (\vec{v} \cdot \nabla T)\right) = \theta_m \nabla^2 T + H_{lv}\dot{n}''' \quad (3)$$

$$\frac{\partial c}{\partial t} = \nabla \cdot (D\nabla c + D_T \nabla T) - \vec{v} \cdot \nabla c - \dot{n}''' \quad (4)$$

where $\rho_m$ is gas mixture density, $\mu_m$ is gas mixture viscosity, $C_{p,m}$ is gas mixture heat capacity, $\theta_m$ is gas mixture thermal conductivity, $H_{lv}$ is condensation latent heat of condensing species, D is diffusion constant of dilute species in gas mixture, and $D_T$ is thermodiffusion (Soret) coefficient. The source term $\dot{n}'''$ is the volumetric condensation rate of the condensing species. This term can be added to both the heat diffusion and the dilute species transport equation to capture the phenomenon of droplet formation in supersaturated region. The value of $\dot{n}'''$ can be calculated by using classic nucleation theory:

$$\dot{n}''' = \frac{4\pi\rho_l r^{*3} J}{3M_r} \quad (5)$$

$$r* = \frac{2\sigma v_m}{kT \ln S} \quad (6)$$

$$J = \sqrt{\frac{2\sigma}{\pi m_l}}\, v_l \left(\frac{P_v}{kT}\right)^2 \exp\left\{-\frac{16\pi v_m^2 \sigma^2}{3(kT)^3(\ln S)^2}\right\} \quad (7)$$

$$S = \frac{P_v}{p_{sat}} \quad (8)$$

where J is nucleation rate of water droplet, r* is the critical droplet radius, $M_r$ is molar mass of condensing species, $\rho_l$ is the density of condensing species in liquid phase, σ is the surface tension between gas mixture and condensate droplet, mi is mass of one molecule of condensing species, $v_l$ is volume occupied by one condensate molecule, k is Boltzmann constant. $P_v$ is partial vapor pressure of condensing species. Assuming the exhaled breath behaves like ideal gas, the partial pressure can be calculated using following equation:

$$P_v = cRT \quad (9)$$

where R is universal gas constant. The saturated vapor pressure ($P_{sat}$) can be calculated by using Antoine equation:

$$p_{sat} = 133.32 \times 10^{C_1 - \frac{C_2}{C_3 + T(K)}} \quad (10)$$

In addition to the four governing equations, to account the deposition by the diffusion of droplet particle, the concentration of droplet particle (N) can also be calculated by solving the particle field differential equation:

$$\frac{\partial N}{\partial t} = D_p \nabla^2 N - \nabla v_{th} N + J \quad (11)$$

where $D_p$ is diffusion coefficient of droplet particle, $v_{th}$ is thermodiffusion coefficient of the droplet particle.

The boundary conditions can be applied in accordance with differential equations that can be solved. For the mass conservation and Navier-Stokes's equation, a no-slip condition (v=0) can be applied at the subcooled wall and atmospheric pressure (P=1 atm) can be applied at the outlet of the channel. The dilute species can be at saturation at the subcooled wall gas liquid interface, thus:

$$c_i = c_{sat} = \frac{RT}{P_{sat}} \quad (12)$$

Based on this boundary condition, the amount of vapor condensing to the thin film can be calculated as:

$$\dot{n}''\left(1 - \frac{c_i R T_i}{P}\right) = D\nabla c_i \quad (13)$$

The latent heat contribution of this condensation process to the heat transfer equation is modelled as boundary heat source:

$$q''_{latent} = H_{lv}\dot{n}'' \tag{14}$$

If the contribution from suspended droplet is included, the subcooled wall boundary condition and the deposited droplet can be respectively calculated using following equation:

$$N_i = 0 \tag{15}$$

$$\dot{n}''_{particle} = \frac{4}{3}\pi r^{*3}\rho_l D_p \nabla N_i \tag{16}$$

Figure 4:
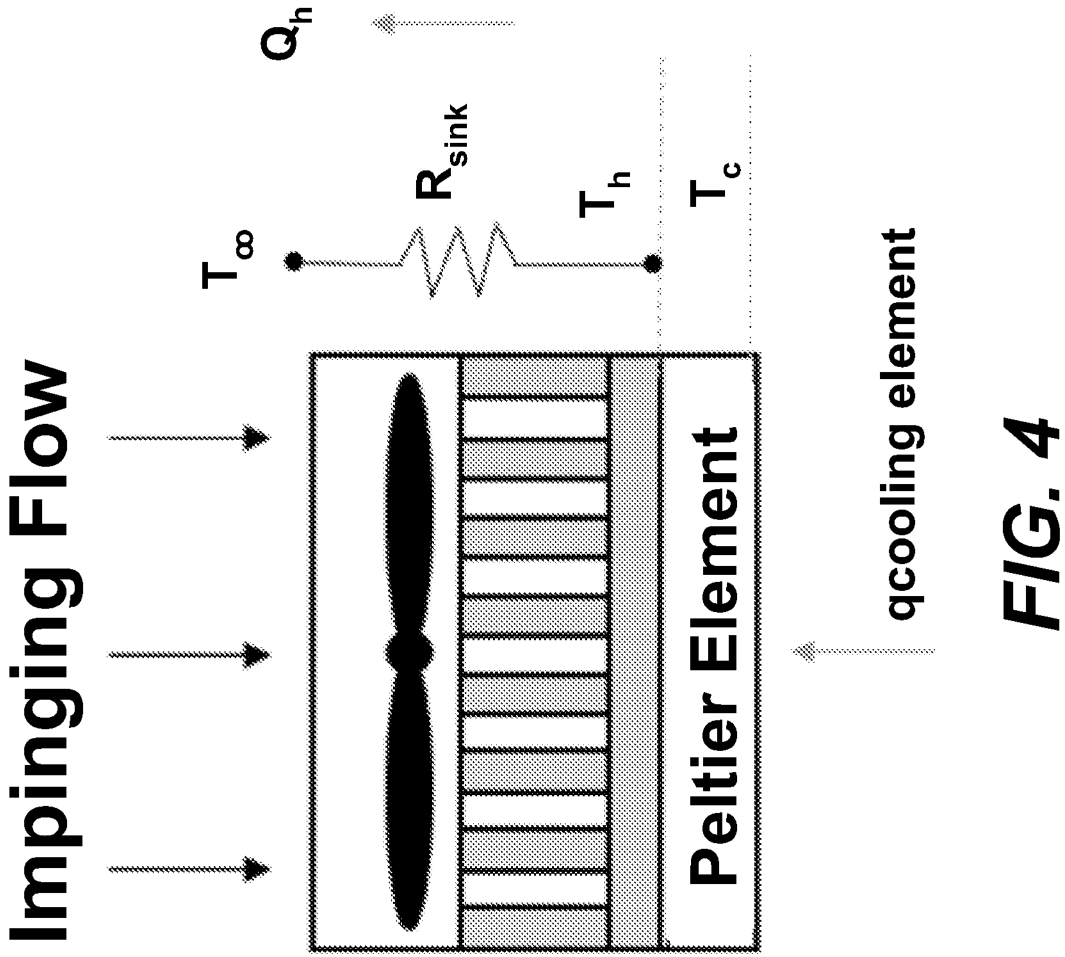
FIG. 4 illustrates a cooling plate in a vapor analysis system in accordance with the present disclosure.

The cooling method used to sub-cool the condenser wall can be a Peltier cooler that is enhanced with a fan and heatsink system (FIG. 4). The Peltier cooler boundary condition can be applied to solve the heat diffusion equation and has following mathematical relation:

$$q_w = AT_w + B \tag{17}$$

where A and B are constants that depend on the properties of peltier element: Seebeck coefficient ($S_c$), electrical resistance ($R_{elec}$), thermal conductance ($K_{ther}$), applied current (I), and the thermal resistance of heatsink system with impinging flow ($R_{sink}$[8]. Mathematically, the value of A and B can be calculated as follows:

$$A = \left(S_c I + K_{ther} - \frac{K_{ther}^2 R_{sink}}{(1 - S_c I\, R_{tot} + K_{ther} R_{sink})}\right) \tag{18}$$

$$B = -\left(\frac{K_{ther} R_{sink}}{(1 - SIR_{sink} + K_{ther} R_{sink})} + 1\right)\frac{I^2 R_{elec}}{2} - \left(\frac{K_{ther}}{(1 - S_c IR_{sink} + K_{ther} R_{sink})}\right)T_\infty \tag{19}$$

For two stacked Peltier coolers, A and B values can be calculated as follows:

$$A = \left(S_C I_1 + K_{ther} - \frac{K_{ther}^2}{(S_c(I_2 - I_1) + 2K_{ther})} - \frac{1}{M}\left[\frac{K_{ther}^2}{(S_c(I_2 - I_1) + 2K_{ther})}\right]^2\right) \tag{20}$$

$$B = -\frac{I_1^2 R_{elec}}{2} - \left\{\frac{K_{ther}^2}{(S_c(I_2 - I_1) + 2K_{ther})}\left[\frac{(I_1^2 + I_2^2)R_{elec}}{2K_{ther}}\right]\right\} - \left\{\frac{K_{ther}^2}{M(S_c(I_2 - I_1) + 2K_{ther})}\left[\frac{I_2^2 R_{elec}}{2} + \frac{K_{ther}}{(S_c(I_2 - I_1) + 2K_{ther})}\left[\frac{(I_1^2 + I_2^2)R_{elec}}{2}\right] + \frac{T_\infty}{R_{sink}}\right]\right\} \tag{21}$$

$$M = \left(\frac{1}{R_{sink}} - SI_2 + K_{ther} - \frac{K_{ther}^2}{(S(I_2 - I_1) + 2K_{ther})}\right) \tag{22}$$

where subscript 1 indicates the Peltier cooler at the cold side (in contact with channel wall) and subscript 2 indicates the hot side Peltier (in contact with the heatsink).

For the condenser channel, a plain channel with rectangular cross section can be selected. The length, width, and thickness of the channel can be selected to maximize the amount of water vapor removed from the breath sample. Mathematically, a parameter called water removal efficiency (n) can be used to quantify the removal quality:

$$\eta = \frac{c_{in} - c_{out}}{c_{in}} \tag{23}$$

Figure 5A:
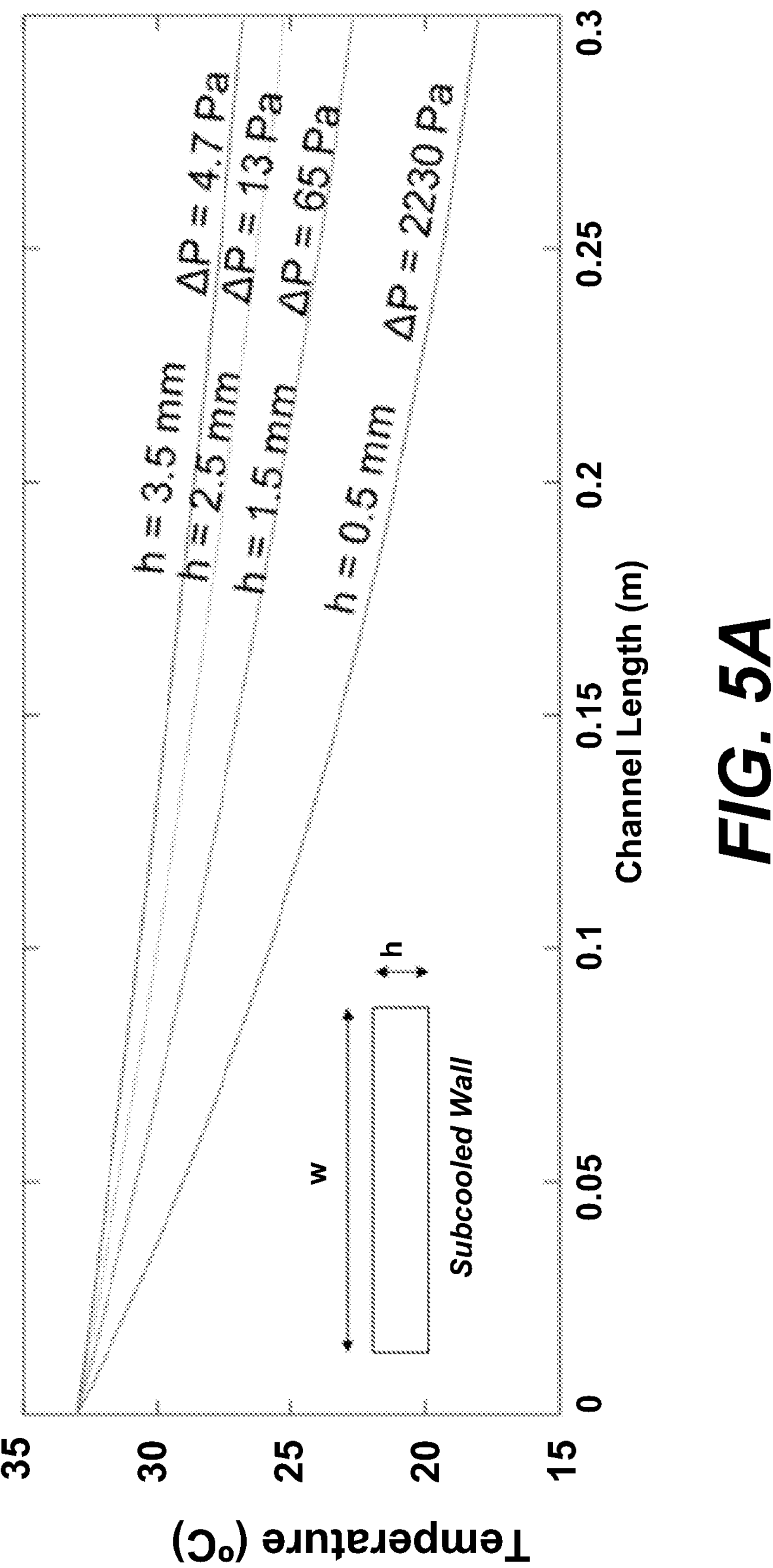
FIGS. 5A & 5B illustrate plots of average temperature and liquid concentration for various channel lengths in a vapor analysis system in accordance with the present disclosure.
Figure 5B:
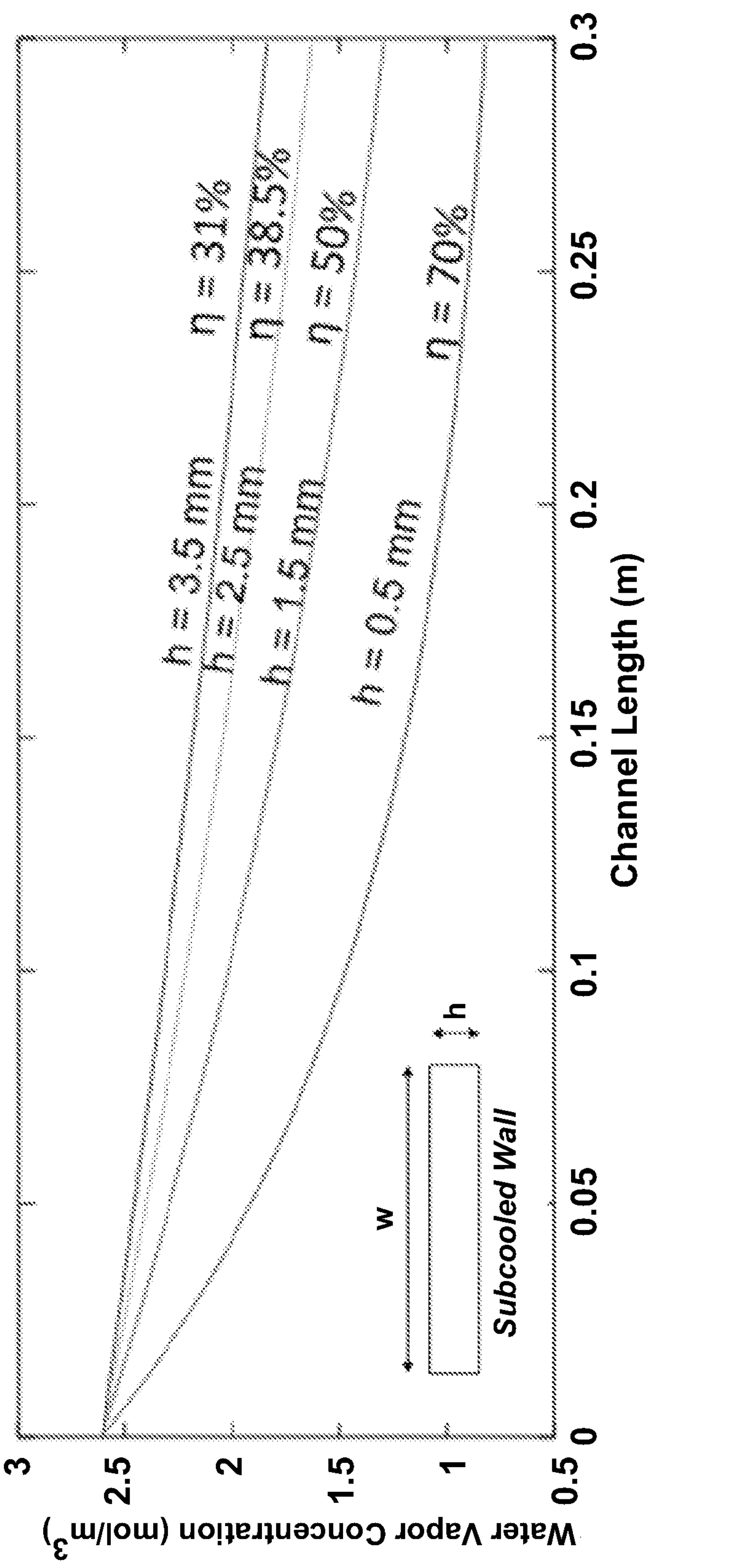
Figure 6:
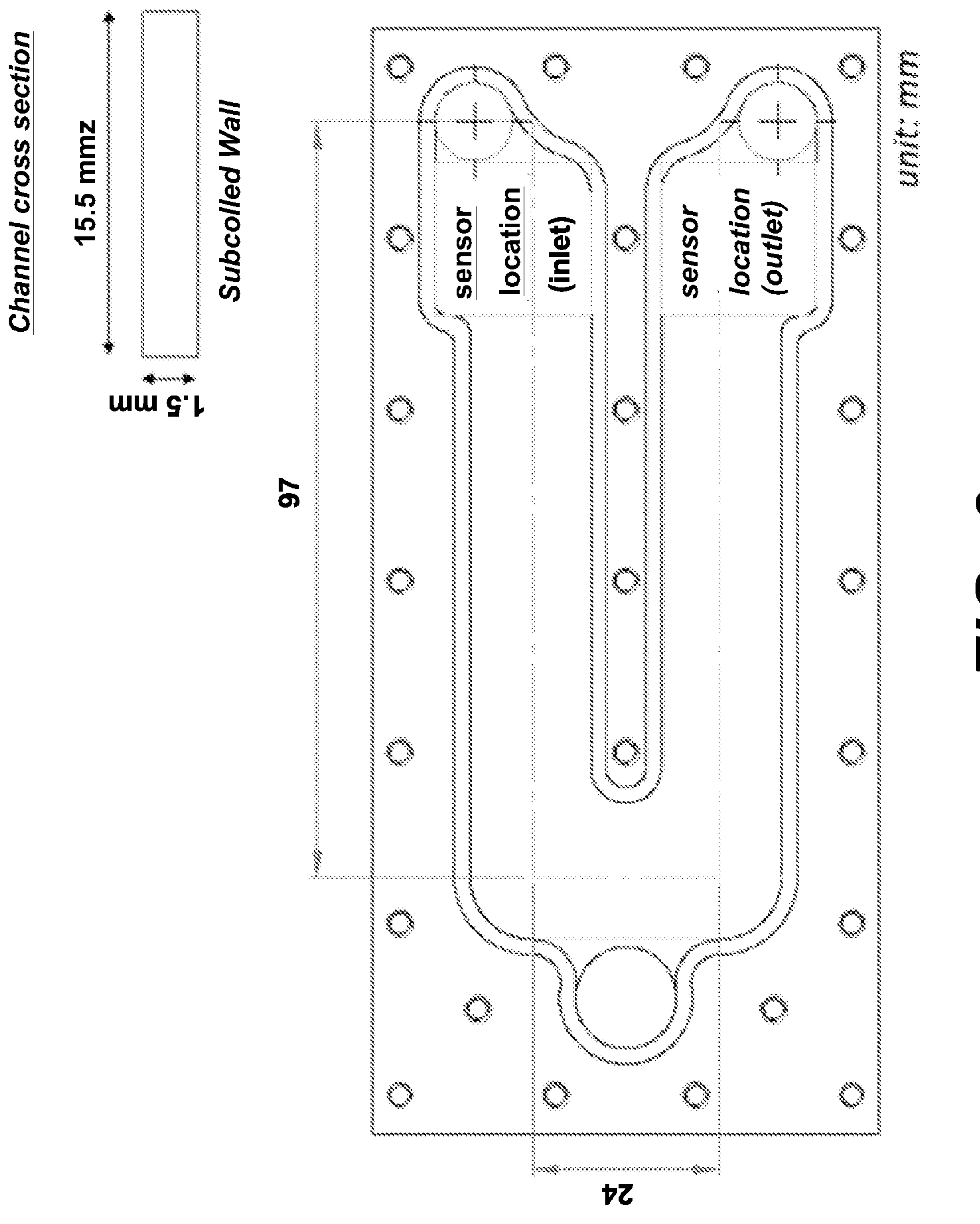
FIG. 6 illustrates a top-down view of an example vapor analyzer in accordance with the present disclosure.
Figure 7:
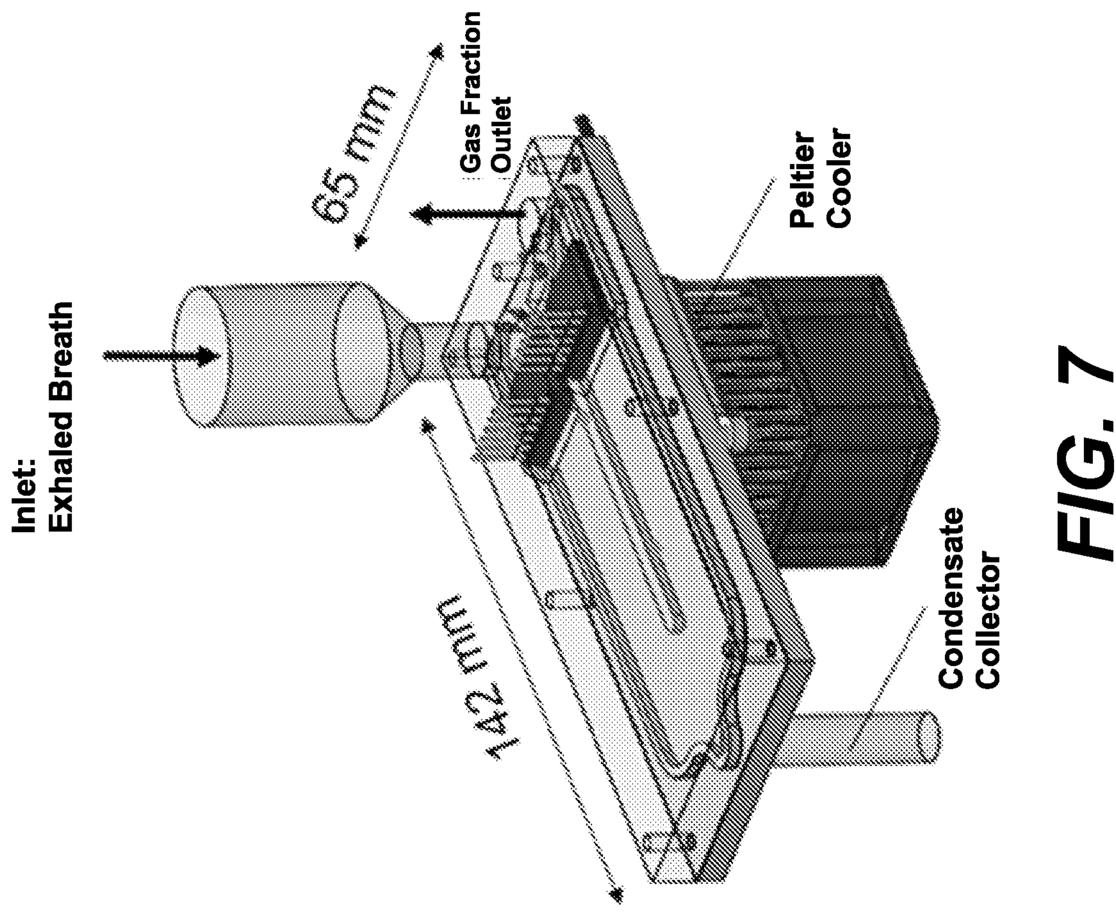
FIG. 7 illustrates an isometric view of an example vapor analyzer in accordance with the present disclosure.
Figures 8A, 8B:
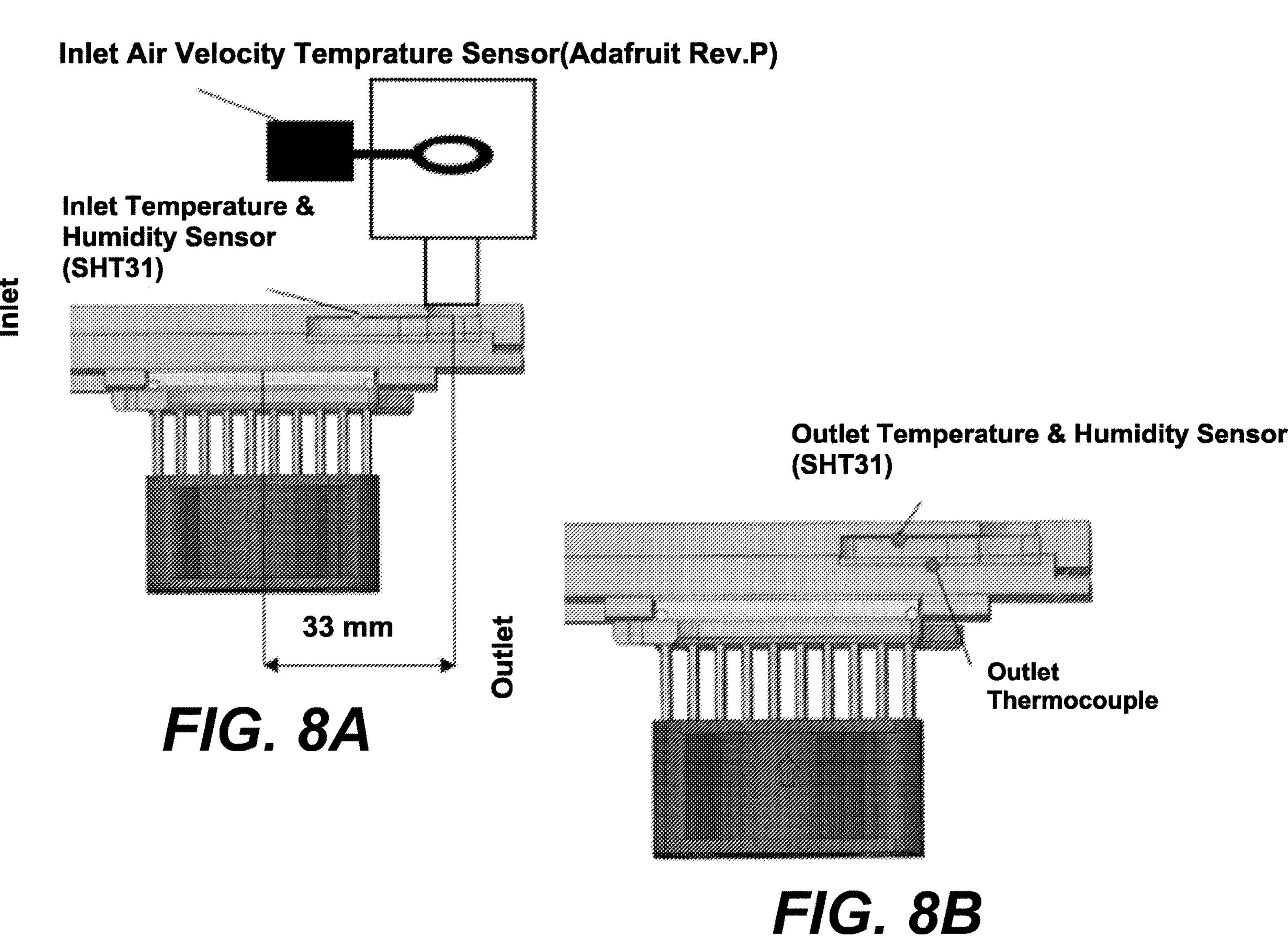
FIGS. 8A & 8B illustrate side views of an example vapor analyzer in accordance with the present disclosure.

A removal efficiency of 95% and 99.5% can be achieved by cooling down the bulk temperature of exhaled breath sample to −10° C., and −40° C., respectively. However, the geometry of the condenser can play an important role to the deviation of bulk temperature of the breath flow to the prescribed subcooled surface temperature. FIGS. 5A & 5B show the average fluid temperature and water vapor concentration of the rectangular channel versus channel length for different channel thickness. Essentially, a longer channel can have a better removal efficiency, although at some point the channel temperature can reach subcooling temperature and no more water vapor will condense. The channel thickness can be a desirable parameter to shorten the channel length to achieve this terminal temperature, the smaller the channel thickness the faster the temperature and vapor concentration decreases. However, as the channel thickness is reduced, the pressure drop can increase significantly, making the breathing process through the channel more uncomfortable and even potentially damaging to a lung for prolonged use. A standard for respiratory protective device, such as EN149, recommends a pressure drop lower 300 Pa at 160 L/min (equivalent with pressure resistance of 112.5 Pa·s/L) to ensure the breath comfort. In addition, the channel length can be minimized to have the system in handheld dimension range for Point of Care application.

After further optimization, a condenser channel with the dimensions shown in FIG. 6, FIG. 7, and FIGS. 8A & 8B can be used as an illustrative example. The condenser channel can be made of 6 mm-thick aluminum 6061 sheet and the channel lid made of Acrylic (McMaster Carr). The channel and the lid can be fastened and sealed using a 2 mm thick cork gasket sheet (McMaster Carr) to minimize the leakage. A humidity and Temperature Sensor SHT31D (Adafruit) can be attached both at the inlet and outlet, and a thermocouple can be placed at the outlet surface to measure the condenser wall temperature. For in vivo analysis, an air velocity sensor Rev.P (Adafruit) can be attached at the inlet to measure the breath flowrate. The channel can be cooled by a 40×40 mm single stage thermoelectric element (CUI CP85438) and connected to a pin-fin heatsink (FSR40, Alpha Novatech) that can be cooled by a fan with two different powers: Low power fan (Cofan M45; 12 V, 0.18 A) and high-power fan (Delta THA0412BN; 12 V, 0.89 A). With this cooling system, three configurations can be arranged to achieve different channel temperature: (1) One Peltier element with low power fan, (2) One Peltier element with high power fan, and (3) Two Peltier element (stacked) with high power fan. The detail about thermoelectric constants and achievable surface temperature for these three configurations are listed in Table 1.

TABLE 1

Peltier element configurations and parameters

| Config. | Number of Peltier | Fan | Peltier Element Current (A) | Peltier Element Constant A (W/K) | Peltier Element Constant B (W) | Steady State Channel Surface Temperature (±0.3° C.) |
|---|---|---|---|---|---|---|
| 1 | 1 | Type 1 | 1.7 | 0.300 | −85.6 | 16.5° C. |
| 2 | 1 | Type 2 | 2.5 | 0.396 | −110.14 | 11.5° C. |
| 3 | 2 (Stack) | Type 2 | 1.65 (cold side) 2 (hot side) | 0.269 | −72.91 | 8.5° C. |

S = 0.03203 V/K
$R_{elec}$ = 1.5604 Ω
$K_{ther}$ = 0.58514 W/K
$R_{sink}$ = 58 K/W (Low power fan); 105 K/W (High power fan)

Figure 9:
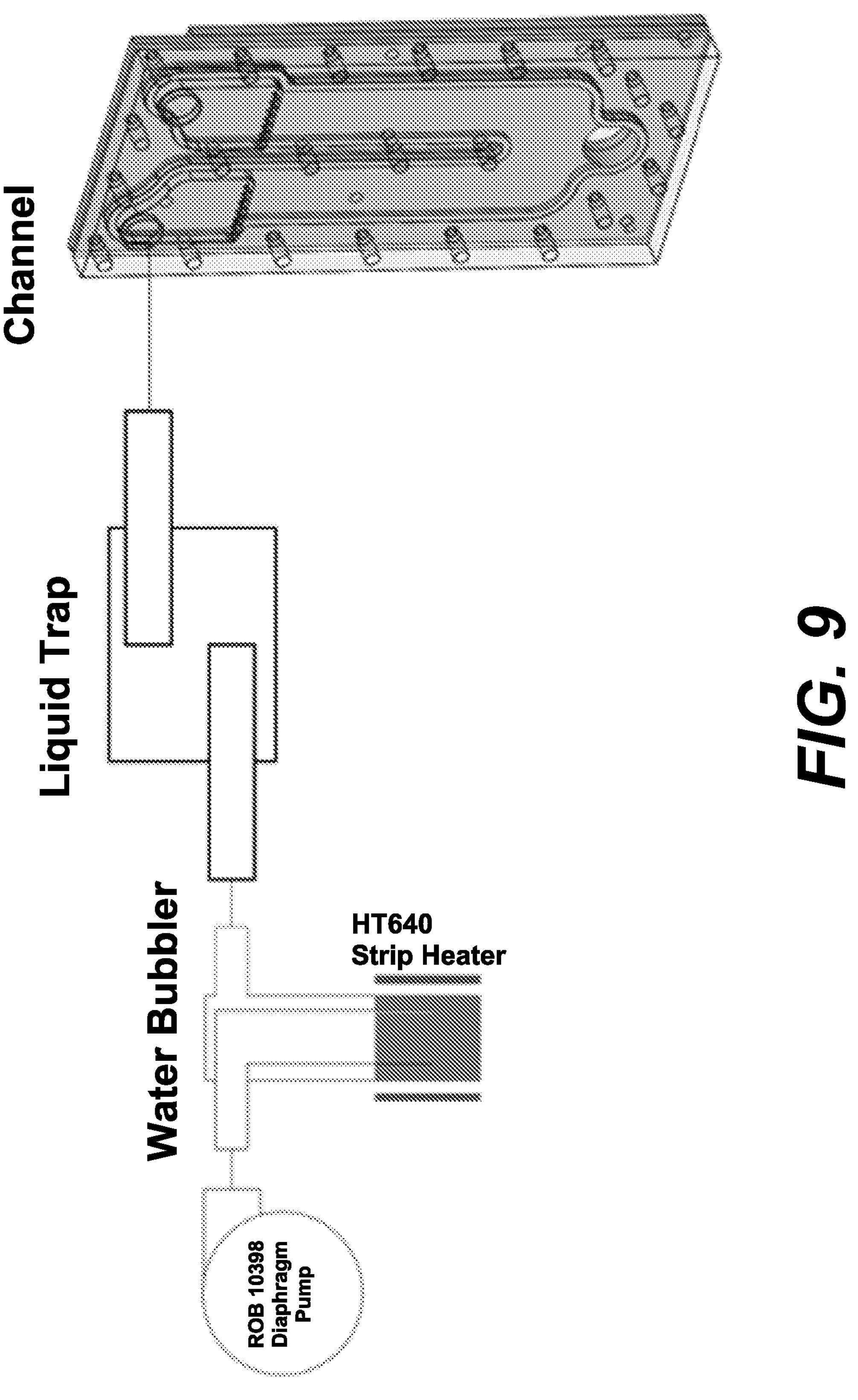
FIG. 9 illustrates a block diagram of an example vapor analysis system in accordance with the present disclosure.
Figures 10A, 10B:
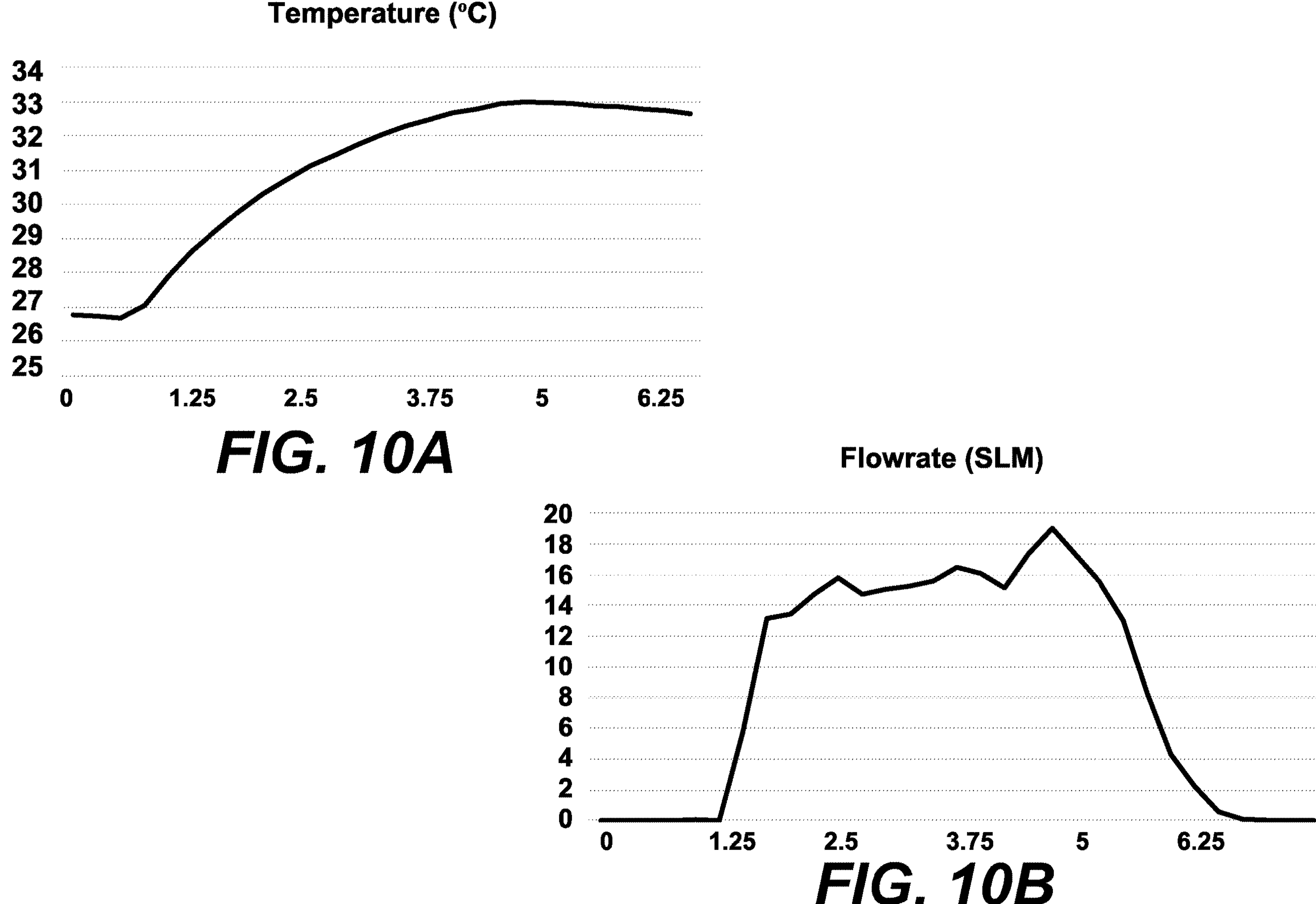
FIGS. 10A-D illustrate plots of various sample properties over time for a vapor sample in accordance with the present disclosure.
Figures 10C, 10D:
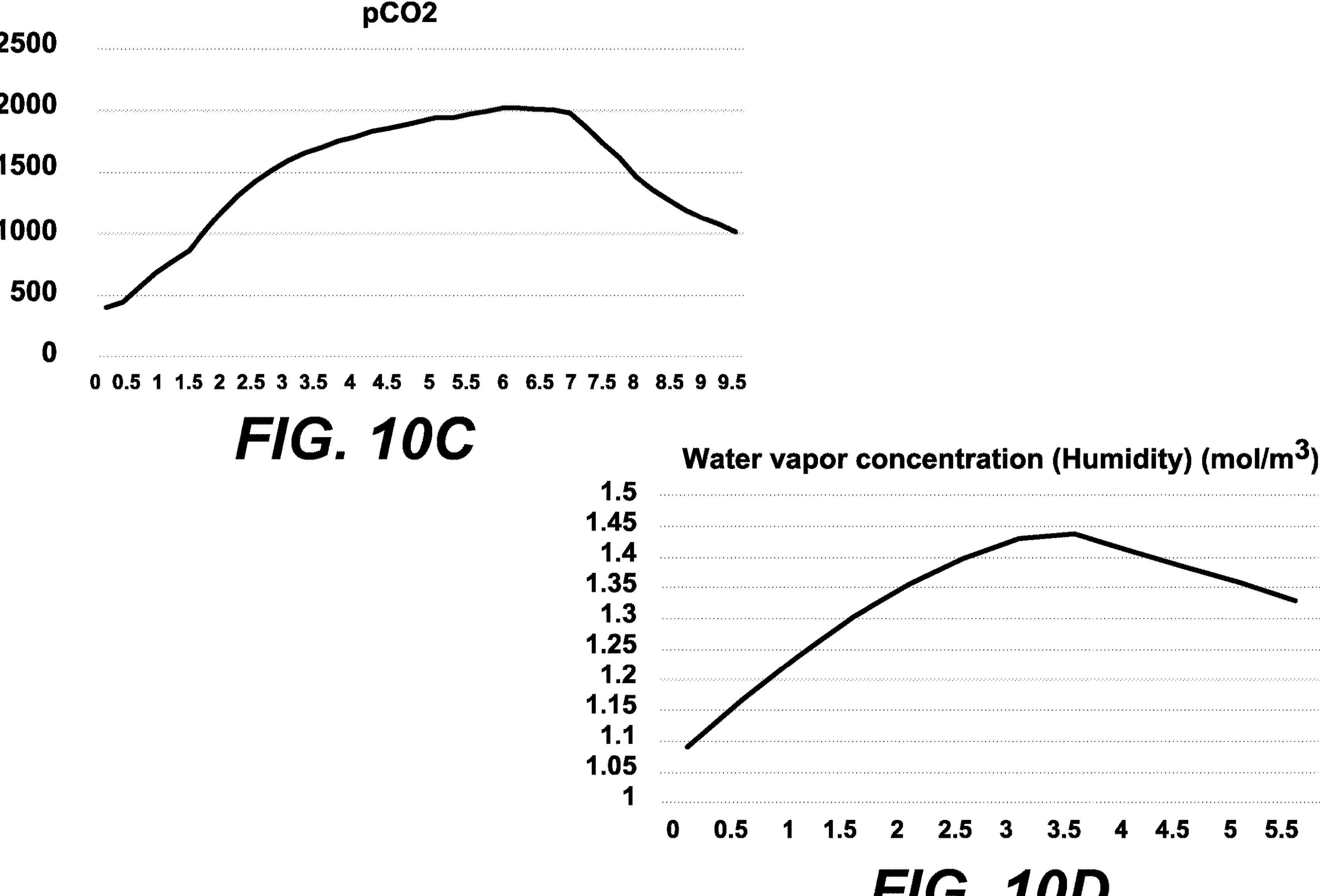

The in vitro experiment can be carried out to validate the mathematical model for the breath condensation analysis simulation. In this experiment, a warm humid air can be generated artificially with the setup shown in FIG. 9. A diaphragm pump (ROB 10398) can be used to blow air with a constant volume flow rate of 5.2 L/min (8V). The air pumped by the diaphragm pump can pass through a water bubbler (Ace Glass Inc., 24/40) filled with warm water heated using a strip heater (HT640). This can produce near saturated air (RH 98%±0.9%) with temperature ranging from 23 to 31° C. Between the bubbler and condenser channel, a liquid trap (Alcopro disposable breathalyzer square mouthpiece) can be placed to contain the condensing liquid along the pipe so that it will not enter the condenser. The temperature and humidity can be measured using a SHT31D sensor at the inlet and outlet, and the condensate can be collected in a vial and measured using precision weight scale (Ohaus Explorer).

The in vivo experiment can be carried out using actual exhaled human breath for input. In addition to the sensors equipped in the in vitro test, an air velocity sensor (Rev.P) can be attached at the condenser inlet to check the profile and variability of the exhaled breath volume flow rate. For each collection, the respondent can be asked to take a deep breath and exhale for as long as possible (Expiratory Reserve Volume). The profiles of the flowrate, temperature, carbon dioxide, and humidity are shown in FIGS. 10A-D. In this experiment, ten exhalation cycles can be selected for each experiment. This value can be selected based on the reasonable number of exhalation cycle of a person below 10 minutes and can produce significant enough amount of condensate for measurement. In addition, it is worth noting that a condensate buildup can occur due to the hydrophilic nature of the condenser material used (aluminum). In more exhalation cycles, this could result in inaccuracy of the model prediction and potentially damage the humidity sensor due to flooding. Therefore, careful placement of the humidity sensor as well as having self-cleaning surface can be desirable for prolonged use.

Figures 11A, 11B:
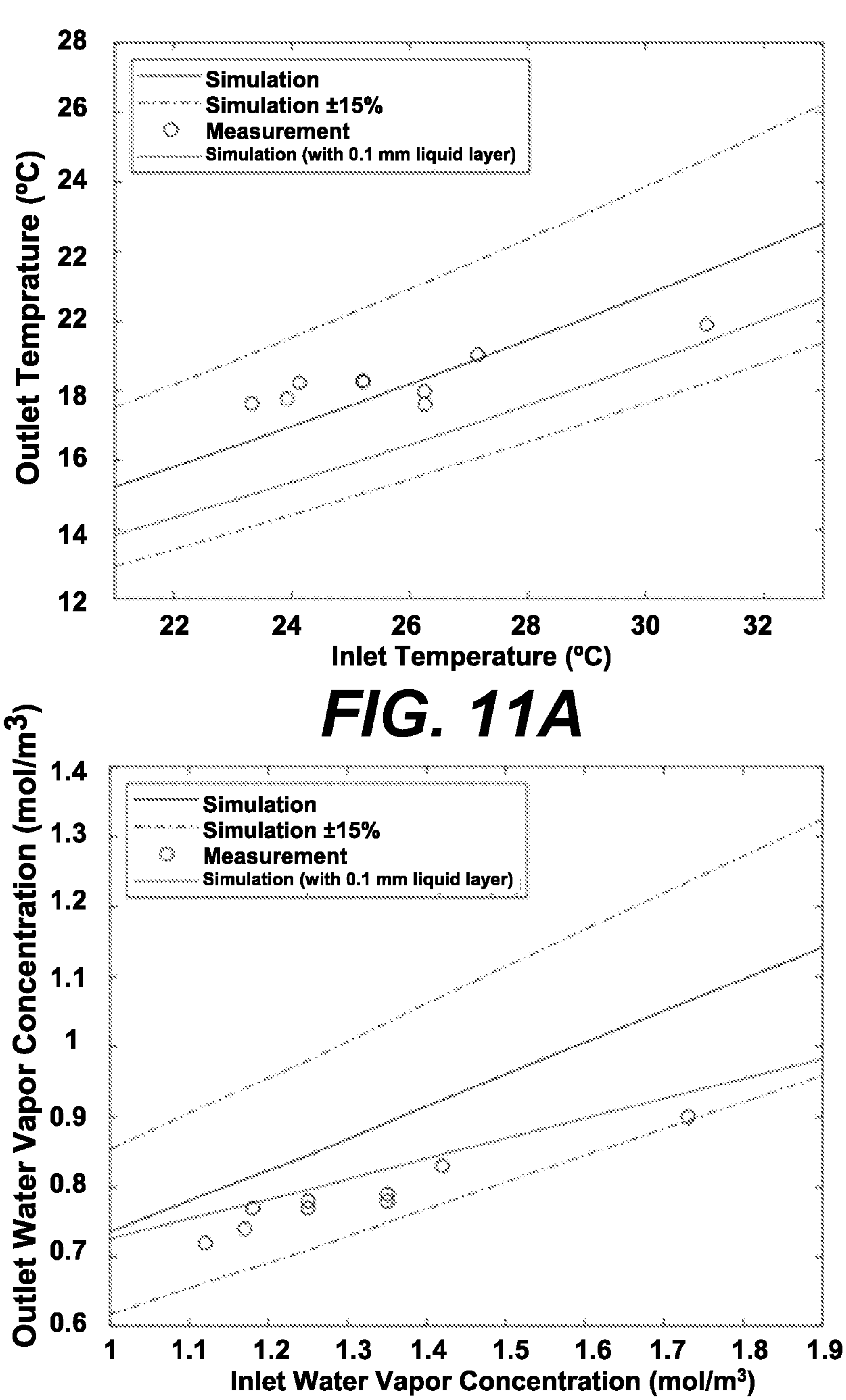
FIGS. 11A-C illustrate plots of outlet parameters detected for an example vapor analysis system in accordance with the present disclosure.
Figure 11C:
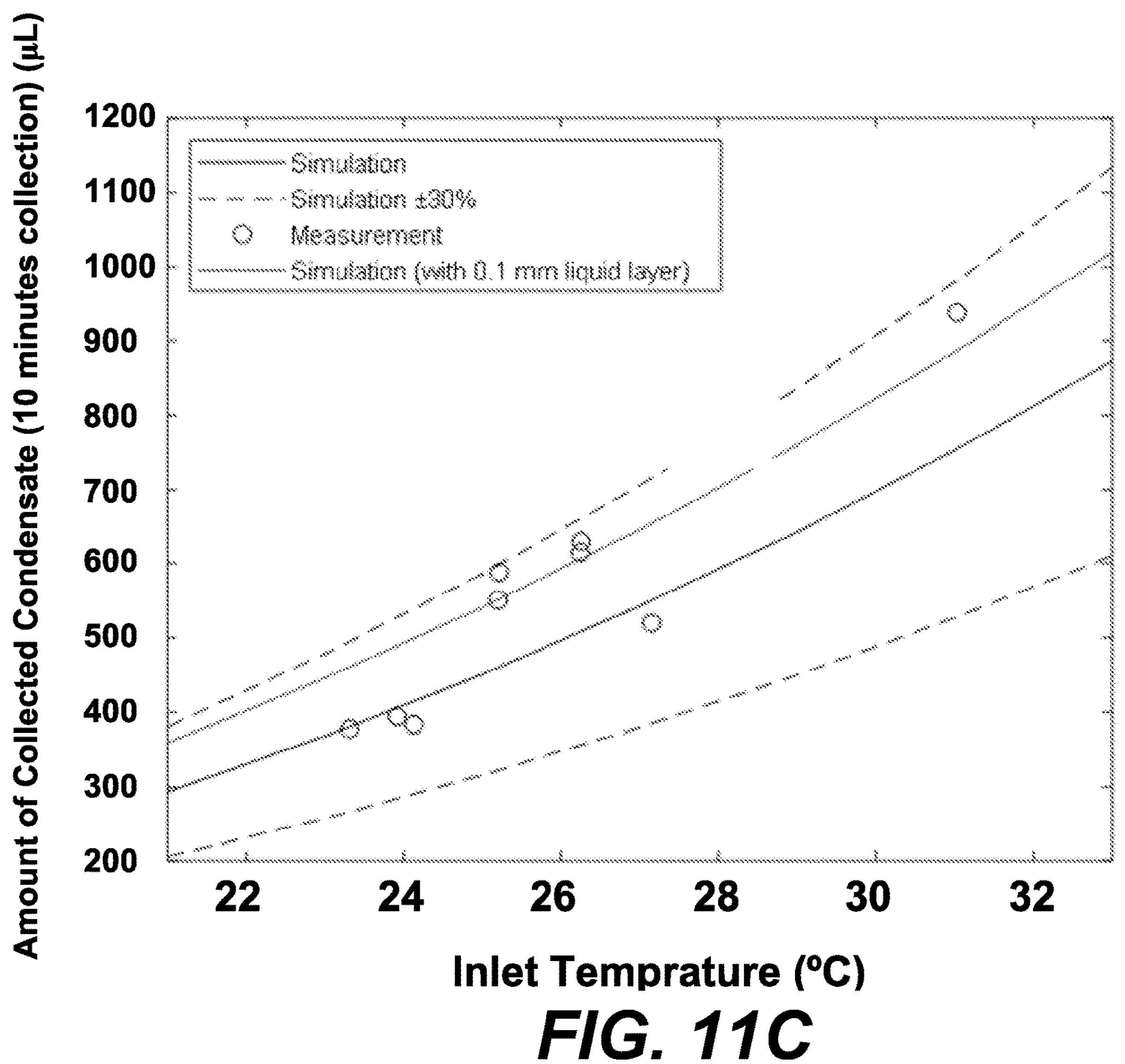
Figure 12A:
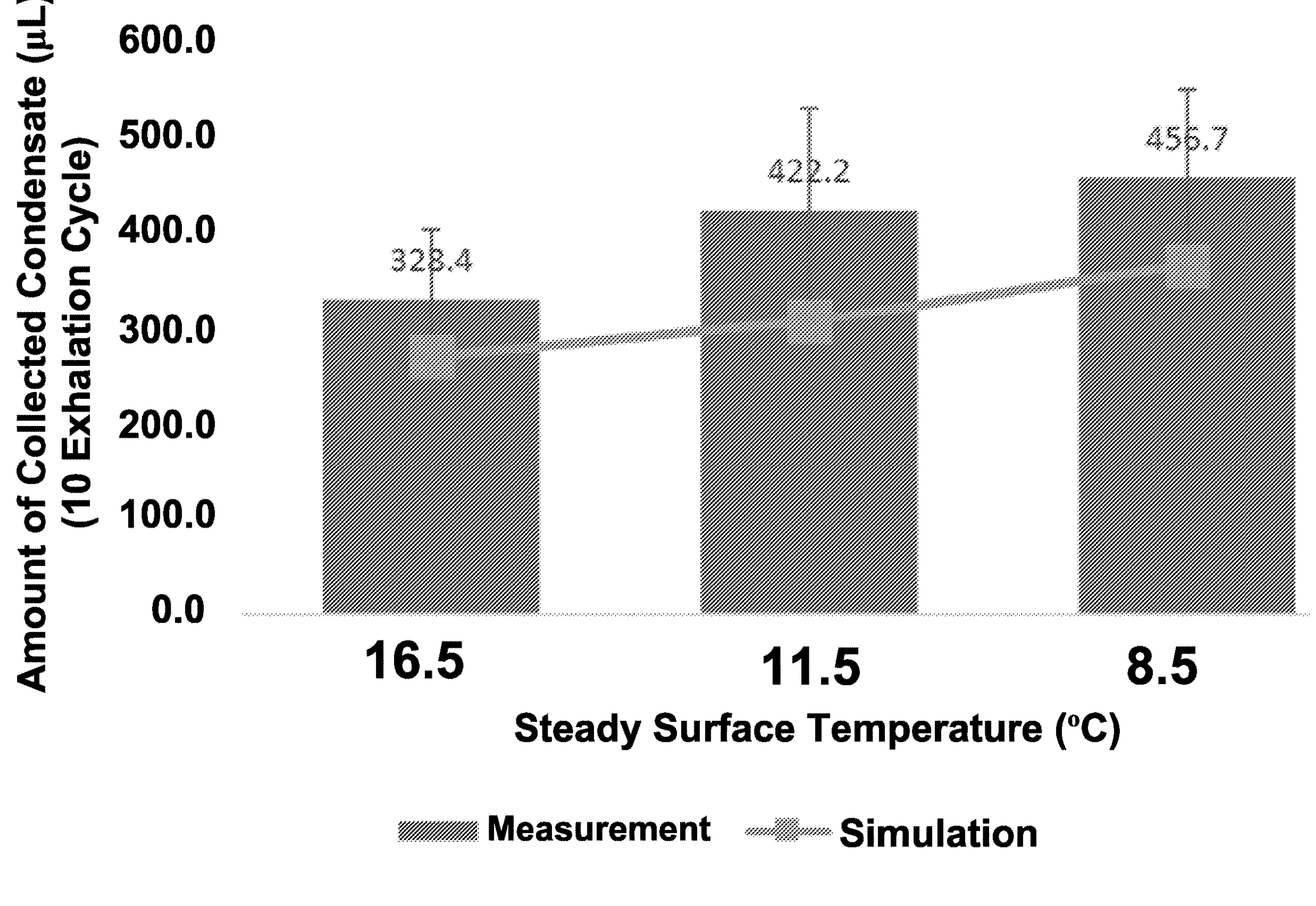
FIGS. 12A & 12B illustrate additional plots of outlet parameters detected for an example vapor analysis system in accordance with the present disclosure.
Figure 12B:
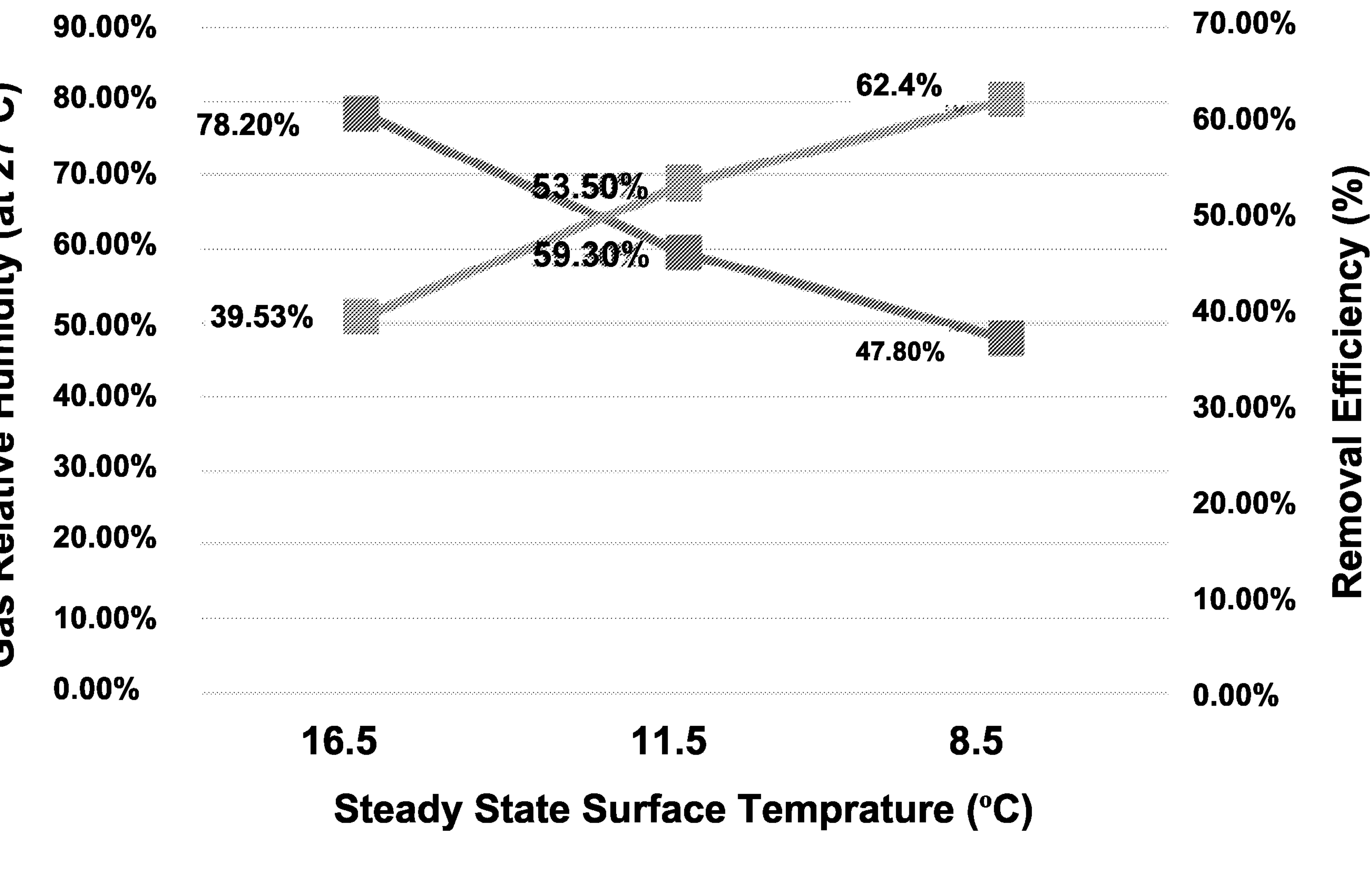
Figure 13:
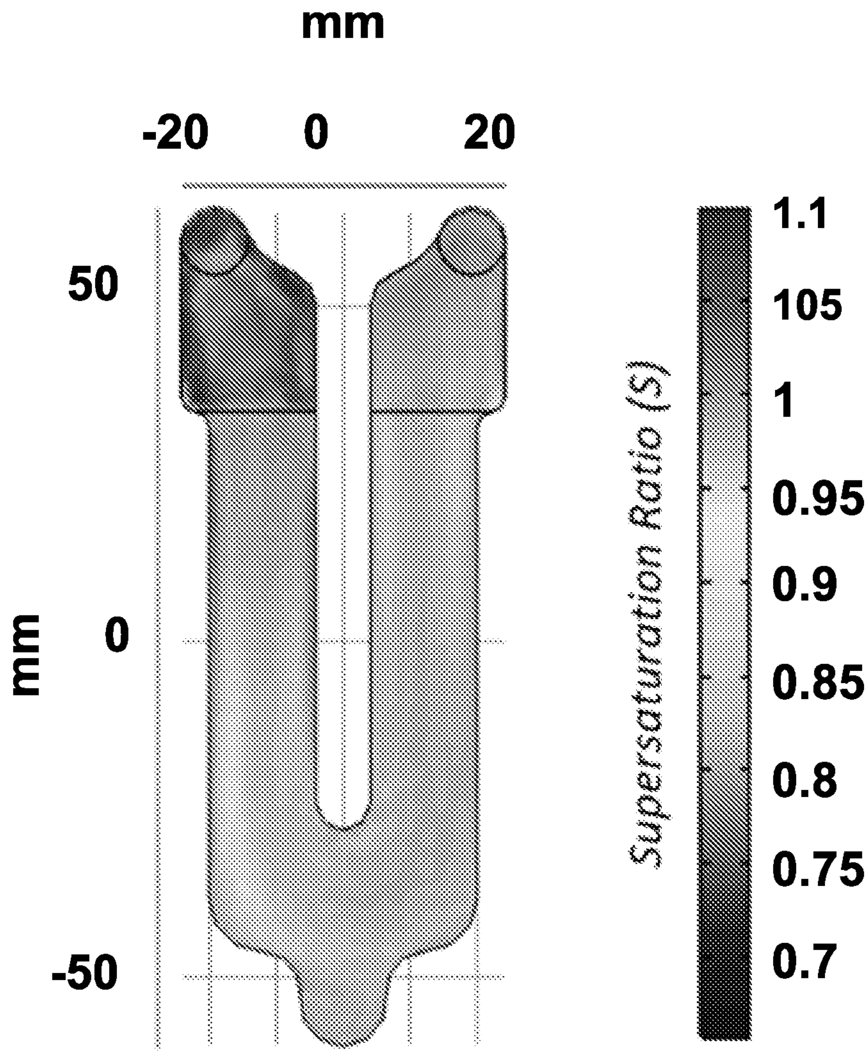
FIG. 13 illustrates a plot of supersaturation ratio for an example vapor analyzer in accordance with the present disclosure.

The results for in vitro test are shown in FIGS. 11A-C, and the results for the vivo test are shown in FIGS. 12A & 12B. Based on the in vitro experiment, the simulated value of temperature and water vapor concentration can have a good agreement with the measurement with deviation less than 10% and the collected condensate with deviation less than 30%. Moreover, the calculated supersaturation ratio across the channel (FIG. 13) can be smaller than 1.1 in which a metastable droplet is barely formed, and the classical nucleation theory formula can give a vanishingly small nucleation rate (J) value.

It is noted that the model can underestimate the value of collected condensate and, consequently, overestimate the water vapor concentration at the outlet. This tendency can be consistent in both in vitro and in vivo experiments. Without wishing to be bound by any particular scientific theory, this phenomenon can be caused by the contribution of suspended fine droplets in the breath sample to the condensate deposition and/or a mass transfer enhancement in the presence of deposited droplet on the subcooled surface. An exhaled human breath can contain suspended water droplets ranging from 0.1-8 μm with concentrations ranging from 0.001-12 $cm^{-3}$. Assuming maximum size and concentration of suspended droplets and assuming all the droplets are deposited on the condensed surface, given the flowrate condition on the in vivo test, the amount of condensate collected from the suspended droplet can be 63 uL which can be 19% of the total collected condensate.

Figure 14:
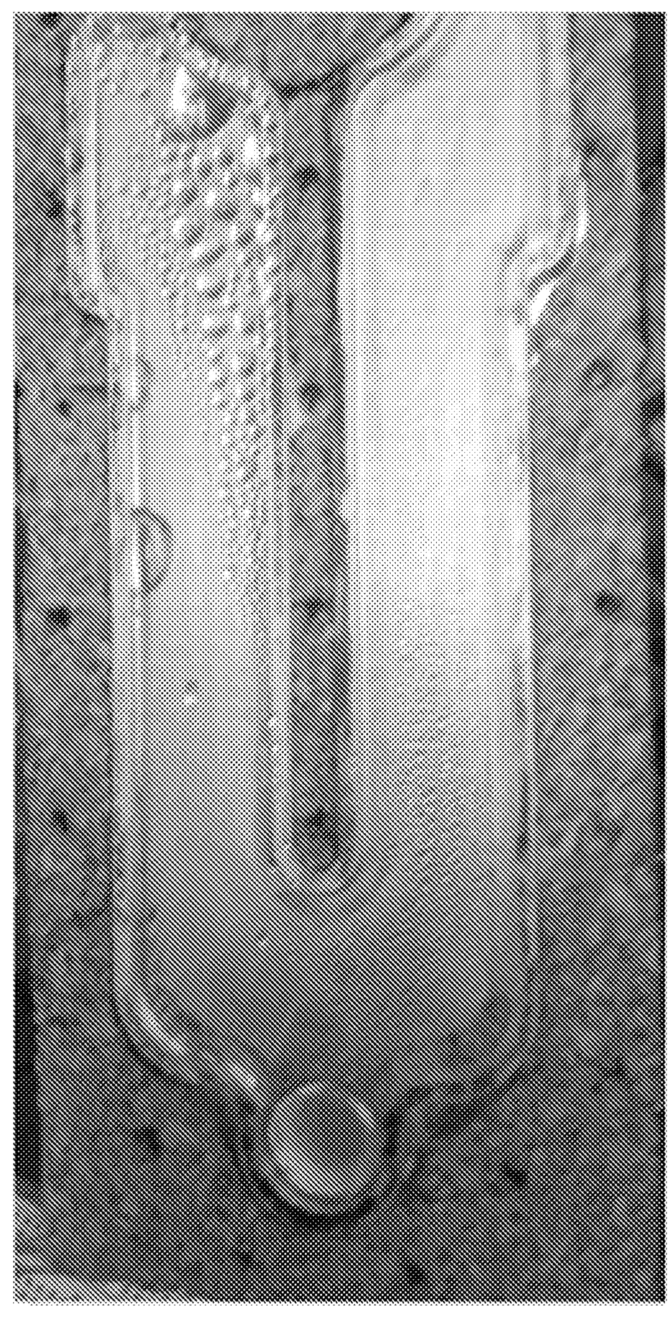
FIG. 14 is a photograph of an example vapor analyzer in accordance with the present disclosure.

On the other hand, while it increases the heat transfer resistance, the droplet build-up on subcooled surface can also shorten the distance between the bulk fluid to the condensate surface and can make the vapor diffuse faster. A simulation using 0.2 mm pre-deposited liquid film can be carried using the model (FIGS. 12A & 12B), and the result can indicate more condensate was collected in the presence of liquid film. This can be supported with the experiment result in which the condensate droplet kept sticking to the surface until it reached the droplet departure thickness that is in the same order of magnitude with the channel thickness (FIG. 14). Without wishing to be bound by any particular scientific theory, this can indicate that having a self-cleaning surface can be disadvantageous for the amount of condensate collected. The good agreement between the simulated and measured value can indicate promising potential for the model to simulate multicomponent mixture simulation and predicting the presence of trace biomarker in gas and liquid portion.

The breath collection performance of the designed channel is shown in FIGS. 12A & 12B, based on in vivo test. The removal efficiency of the condenser system can increase as the surface temperature decreases. At surface temperature of 8.5° C., corresponding on Peltier element configuration 3 (Table 1), removal efficiency of the condenser can be 62.4%. With this configuration, the condenser can provide less humid gas portion of breath sample with water vapor content of 0.703 mol/$m^3$, equivalent with RH 47.8% at 27° C. At the same time, the amount of condensate collected by the condenser can be 0.457±0.092 ml. The standard deviation in the collected condensate can be 0.091 mL on average, which can result from the variability of the exhaled breath profile and the unpredictable condensate droplet motion within the channel. In this case, the channel can be made of hydrophilic aluminum, which can allow condensate droplet build-up to a considerable size for random droplet collision to happen before departing (FIG. 14). On the other hand, the hydrophilic surface can also retain smaller condensate droplets that cannot be collected. Modifying the condenser surface to have a high hydrophobicity and low droplet hysteresis can resolve this issue, as well as further features to satisfy a self-cleaning example of a breath collection system.

While the present disclosure has been described in connection with a plurality of exemplary aspects, as illustrated in the various figures and discussed above, it is understood that other similar aspects can be used, or modifications and additions can be made to the described aspects for performing the same function of the present disclosure without deviating therefrom. For example, in various aspects of the disclosure, methods and compositions were described according to aspects of the presently disclosed subject matter. However, other equivalent methods or composition to these described aspects are also contemplated by the teachings herein. Therefore, the present disclosure should not be limited to any single aspect, but rather construed in breadth and scope in accordance with the appended claims.

What is claimed is:

1. A vapor analyzer comprising:

feeding means configured to feed an analyte in the vapor phase to a chamber defining an interior channel through an inlet in fluid communication with the interior channel;

contacting means configured to contact the analyte with a cooling plate disposed along at least a portion of the interior channel within the chamber;

condensing means configured to condense a portion of the analyte into a liquid portion as a result of contact with the cooling plate, the remainder of the analyte being in a vapor portion;

transferring means configured to transfer:

the liquid portion along a first fluid flow path to a liquid phase outlet; and the vapor portion along a second fluid flow path to a vapor phase outlet;

wherein the liquid phase outlet and the vapor phase outlet are each in fluid communication with the interior channel;

measuring means configured to measure fluid properties along the first fluid flow path and the second fluid flow path; and controller means configured to alter the cooling plate between an active state and an inactive state responsive to the measuring means detecting a particle for detection.

2. The vapor analyzer of claim 1, wherein the first fluid flow path is defined from the inlet, through the interior channel, to the liquid phase outlet;

wherein the second fluid flow path is defined from the inlet, through the interior channel, to the vapor phase outlet; and wherein the first fluid flow path and the second fluid flow path contact the cooling plate.

3. The vapor analyzer of claim 1, wherein at least one of:

the first fluid flow path and the second fluid flow path are parallel; or the first fluid flow path and the second fluid flow path are contained together within the chamber.

4. The vapor analyzer of claim 1, wherein the cooling plate comprises a Peltier cooler.

5. The vapor analyzer of claim 1, wherein the liquid phase outlet is disposed on a surface of the chamber to create an exit from the interior channel; and wherein the cooling plate and the liquid phase outlet share the same surface in the chamber.

6. The vapor analyzer of claim 1 further comprising temperature regulation means configured to regulate the temperature of the cooling plate at a temperature sufficient to condense water vapor from a vapor phase into a liquid phase.

7. The vapor analyzer of claim 1 wherein the cooling plate provides cooling energy to the interior channel in the active state.

8. A vapor analysis method comprising:

feeding an analyte to a chamber defining an interior channel through an inlet in fluid communication with the interior channel, the analyte being in the vapor phase;

contacting the analyte with a cooling plate disposed along at least a portion of the interior channel within the chamber;

condensing a portion of the analyte into a liquid portion as a result of contact with the cooling plate, the remainder of the analyte being in a vapor portion;

transferring the liquid portion along a first fluid flow path to a liquid phase outlet and the vapor portion along a second fluid flow path to a vapor phase outlet, the liquid phase outlet and the vapor phase outlet each in fluid communication with the interior channel;

measuring fluid properties along the first fluid flow path and the second fluid flow path; and altering the cooling plate between an active state and an inactive state;

wherein placing the cooling plate in the active state is responsive to the measuring detecting a particle for detection.

9. The method of claim 8, wherein the cooling plate comprises a Peltier cooler.

10. The method of claim 8, wherein the liquid phase outlet is disposed on a surface of the chamber to create an exit from the interior channel; and wherein the cooling plate and the liquid phase outlet share the same surface in the chamber.

11. The method of claim 8 further comprising maintaining the cooling plate at a temperature sufficient to condense water vapor from a vapor phase into a liquid phase.

12. The method of claim 8 further comprising: providing cooling energy to the interior channel when the cooling plate is in the active state.

13. A vapor analyzer comprising:

a chamber defining an interior channel;

an inlet in fluid communication with the interior channel;

a liquid phase outlet in fluid communication with the interior channel, the liquid phase outlet and the inlet defining a first fluid flow path from the inlet, through the interior channel, to the liquid phase outlet;

a vapor phase outlet in fluid communication with the interior channel, the vapor phase outlet and the inlet defining a second fluid flow path from the inlet, through the interior channel to the vapor phase outlet; and a cooling plate disposed along at least a portion of the interior channel within the chamber such that the first fluid flow path and the second fluid flow path contact the cooling plate;

wherein the vapor analyzer is configured to:

feed an analyte to the chamber through the inlet, the analyte being in the vapor phase;

contact the analyte with the cooling plate;

condense a portion of the analyte into a liquid portion as a result of the contact with the cooling plate, the remainder of the analyte being in a vapor portion;

transfer the liquid portion along the first fluid flow path to the liquid phase outlet;

transfer the vapor portion along the second fluid flow path to the vapor phase outlet;

measure fluid properties along the first fluid flow path and the second fluid flow path;

alter the cooling plate between an active state and an inactive state; and place the cooling plate in the active state responsive to detecting a particle for detection.

14. The vapor analyzer of claim 13, wherein the vapor analyzer is further configured to at least one of:

maintain the cooling plate at a temperature sufficient to condense water vapor from a vapor phase into a liquid phase; or provide cooling energy to the interior channel when the cooling plate is in the active state.

* * * * *